US012471645B2

(12) United States Patent
Groman

(10) Patent No.: US 12,471,645 B2
(45) **Date of Patent: *Nov. 18, 2025**

(54) FLEXIBLE FACE MASK FOR VARIOUS DENTAL AND MEDICAL USES

(71) Applicant: Groman Inc., Margate, FL (US)

(72) Inventor: Boaz Barry Groman, Boca Raton, FL (US)

(73) Assignee: Groman Inc., Margate, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/754,870

(22) Filed: Jun. 26, 2024

(65) Prior Publication Data

US 2024/0415210 A1 Dec. 19, 2024

Related U.S. Application Data

(63) Continuation of application No. 17/324,455, filed on May 19, 2021, now Pat. No. 12,022,898.

(60) Provisional application No. 63/154,673, filed on Feb. 27, 2021, provisional application No. 63/062,383, filed on Aug. 6, 2020, provisional application No. 63/026,730, filed on May 19, 2020.

(51) Int. Cl.

| | |
|---|---|
| ***A41D 13/11*** | (2006.01) |
| ***A61G 10/00*** | (2006.01) |
| ***A61M 16/06*** | (2006.01) |

(52) U.S. Cl.

CPC ...... *A41D 13/1107* (2013.01); *A41D 13/1161* (2013.01); *A61G 10/005* (2013.01); *A61M 16/0694* (2014.02); *A41D 2300/00* (2013.01)

(58) Field of Classification Search

CPC .............. A61M 16/06; A61M 16/0605; A61M 16/0683; A61M 16/0694; A61M 2016/0661; A41D 13/11; A41D 13/1107; A41D 13/1115; A41D 13/1123; A41D 13/113; A41D 13/1138; A41D 13/1146; A41D 13/1153; A41D 13/1161; A41D 13/1169; A41D 13/1176; A41D 13/1184; A41D 13/1192; A41D 2300/00

See application file for complete search history.

(56) References Cited

U.S. PATENT DOCUMENTS 6,450,166 B1 * 9/2002 McDonald .......... A61M 16/085 128/201.22

8,365,734 B1 * 2/2013 Lehman ................ A61B 5/097 128/206.28

(Continued)

*Primary Examiner* — Colin W Stuart

(74) *Attorney, Agent, or Firm* — Gerald E. Linden

(57) ABSTRACT

A flexible mask substrate (MS) with a rigid front plate (FP) which may be a viewing window (VW) causing the mask substrate to extend forward from a patient's face, forming a chamber in front of the patient's mouth. Instrument ports (IP) allow instruments to be introduced through the mask into the patient's oral or nasal cavity to perform dental or medical procedures. An elastic band (CE) on the mask substrate to conform the mask to contours of the patient's face. A malleable metal strip (MM) for conforming the mask to the patient's nose. Methods of fabricating the mask. The mask, and variations thereof, may be used to perform various treatments, including non-oral procedures. Using a nebulizer in conjunction with the mask, wherein the nebulizer is supported independently of the mask by a headband or eyeglasses worn by the patient.

6 Claims, 13 Drawing Sheets instrument port deflector

(56) References Cited

U.S. PATENT DOCUMENTS

| | | | | |
|---|---|---|---|---|
| 12,022,898 | B2 * | 7/2024 | Groman | A61M 15/0021 |
| 2003/0028946 | A1 * | 2/2003 | Zegarelli | A61B 46/00<br>128/857 |
| 2008/0092897 | A1 * | 4/2008 | Behm | A41D 13/11<br>128/206.12 |
| 2017/0007795 | A1 * | 1/2017 | Pedro | A61B 5/082 |

* cited by examiner dental mask with viewing window dental mask with viewing window Step 1 - ‘Flex Cab’ Preparation Step 2 - viewing window attachment Step 3 - fold the 'Flex Cab'

Step 4 - connect side edges

Step 5 - face conforming elastic

Step 6 - fold over

Step 7 - secure face conforming elastic

Step 8 - attach fastening elastic

Step 8 - attach fastening elastic

Dental Mask, front side

Dental Mask, back side malleable metal strip instrument port deflector instrument port deflector instrument port deflector instrument port deflector nebulizer adapter nebulizer supplying aerosolized medication nebulizer supplying aerosolized medication tapered tube mask basic mask (dental)

integrated nose strip (MM) and conforming elastic (CE)

FLEXIBLE FACE MASK FOR VARIOUS DENTAL AND MEDICAL USES

CROSS-REFERENCE TO RELATED APPLICATIONS

This is a continuation of U.S. Ser. No. 17/324,455 filed 19 May 2021 ("parent application")

U.S. Ser. No. 17/324,455 is a nonprovisional of U.S. 63/154,673 filed 27 Feb. 2021

U.S. Ser. No. 17/324,455 is a nonprovisional of U.S. 63/062,383 filed 6 Aug. 2020

U.S. Ser. No. 17/324,455 is a nonprovisional of U.S. 63/026,730 filed 19 May 2020

All of the above are incorporated by reference herein.

FIELD OF THE INVENTION

This invention relates to a flexible face mask, adapted to be worn by a patient, covering the patient's nose and mouth area, while allowing a user (doctor, dentist) to perform a dental or medical procedure involving (interacting with) the patient's mouth or nose. This may include a dental mask, a nasal swab mask, an oral swab mask, an instrument mask, a scope mask, a sinus mask, bronchoscopy and GI endoscopy masks, and also a mask configured for administering nebulizer and breathing treatments.

BACKGROUND

Medical facemasks for delivering oxygen or nebulized treatments to patients are known, and some medical facemasks have filters incorporated therein. For example U.S. Pat. No. 7,559,323 (Hacke, et al.; Jul. 14, 2009; Respan Products, Inc.) discloses a disposable mask assembly with exhaust filter wherein:

- a face mask is provided for a patient that includes a face piece sized to fit over the patient's nose and mouth. The face mask assembly forms a mask chamber between the face piece and the patient's nose and mouth. An inhalation adapter is coupled to the face piece to deliver medication to the chamber. A filter housing is coupled to the face piece and includes a flange section that defines a passageway to connect the mask chamber and the flange section. A filter is positioned in the filter housing. A cover is coupled to the flange section and has an exhalation opening or vent to allow gases from the mask chamber to pass through the filter and escape from the passageway to the atmosphere.

Such medical facemasks are generally semi-rigid, having a contoured shape "out-of-the-box". Some teachings of prior art facemasks may be incorporated into the present invention, such as methods of attaching the facemask to the patient.

The invention(s) disclosed herein may be useful in conjunction with micro-abrasive blasting devices powered by a pressurized-gas source for use with dental procedures, an example of which may be found in U.S. Pat. No. 9,050,156 (2015 Jun. 9; Groman). As noted therein various methods for reducing the overspray of the abrasive are known for such devices. See, for example: U.S. Pat. No. 5,356,292 (1994 Oct. 18; Ho); U.S. Pat. No. 5,197,876 (1993 Mar. 30; Coston); U.S. Pat. No. 6,024,566 (2000 Feb. 15; Bruns et al.). These may disclose add-on splatter guard and collector attachments to air abrasion devices.

In the 2020 Coronavirus pandemic, dental treatments which generate aerosol were halted until evacuation and other aerosol reducing precautions (PPE) were implemented. Treatment options for patients with shortness of breath were limited due to the fear that first line and hospital personnel would be exposed to aerosolized viral particles expelled by patients into the environment. The invention(s) disclosed herein address some of these concerns.

SUMMARY

It is an overall object of the invention to provide an improved facemask (face mask) to be worn by a patient when a user (dentist or doctor) is performing a procedure requiring access to the patient's mouth or nose, while protecting the user from aerosols or particles which are a byproduct of the procedure and/or which are expelled (such as exhaled) by the patient.

It is an object of the invention to provide techniques, including methods and apparatus, for shielding a user (doctor, dentist) from aerosolized particles and the like which may be emitted by a patient during an intraoral procedure such as, but not limited to, micro-abrasive blasting.

Of course, the user can wear a face shield to protect themselves from aerosolized particles and the like which may be emitted by a patient during such an intraoral procedure. However, there are also risks related to the patient "polluting" the immediate environment when such a procedure is being performed as an inevitable direct result of the procedure (such as detritus being spread around) or as a collateral indirect result such as the patient coughing or sneezing. Some hospitals and dental clinics have implemented negative pressure rooms and evacuation devices to draw, collect, and filter the contaminated air in the environment. The facemasks disclosed herein address some of these issues.

The facemask of the present invention is generally a thin, optionally transparent, very flexible mask substrate (or portion) which can easily be deformed to be fitted around the patient's lower face, including nose and jaw. A fastening elastic secures the mask to the patient's face, while a face contour elastic conforms the mask substrate to the contour of the patient's face so that the mask "hugs" the patient's face. The resulting mask may be referred to as a "flex cab".

Various additional elements may be provided on the mask, such as:

- a more rigid (yet substantially planar), very transparent viewing window (or front portion, or plate) disposed on a front portion of the mask substrate, over a view port (opening, cutout) in the mask substrate to allow the user to see into the patient's mouth while performing a procedure or treatment.
- one or more instrument ports in the flexible portion of the mask to allow the user to insert instruments for performing the intraoral or other procedures contemplated herein, such as conventional dentistry (cleaning, filling cavities, etc.), nasal swabbing, oral swabbing, inserting instruments into the patient's oral (mouth) and/or nasal cavities (nostrils) such as for performing specimen collection and various aerosol generating medical procedures, while protecting the user and the immediate environment from aerosols and/or particles which may be byproducts of the procedures or simply the air exhaled by the patient.

In some embodiments, the mask may have two main portions:

- a very flexible mask substrate portion which conform well to the contour of a patient's face, while being lightweight and comfortable to wear; and

- a relatively rigid portion, exemplified by a viewing window, disposed at the front of the mask;
- wherein:
- instrument ports, filters, adapters, etc. can be disposed on the relatively rigid portion; and
- the relatively rigid portion can be moved around by a user to facilitate performing procedures while the flexible mask portion remains fixed in position on the patient's face.

In the main, hereinafter, a dental mask may be described, which has a transparent viewing window disposed on the front surface of the mask substrate. A dental mask may have instrument ports located on either side of the viewing window (in this case, the ports are not located on the viewing window, but rather on the mask substrate). For other (non-dental) uses of the mask, the viewing window may not be required, and may be eliminated or replaced by other features, such as a trap door for selectively allowing a user to access the patient's covered face, instrument ports, and the like.

According to the invention, generally, a dental mask is provided for covering at least the patient's mouth while an oral procedure is being performed. More particularly, the mask may comprise:

- a mask substrate which may be a generally rectangular, flat sheet of a material that is big enough to fit over the patient's lower face (including jaw). This mask substrate should be very flexible to allow the mask to conform well to the contour of the patient's face. The mask substrate need not be transparent.
- a view port (opening) in the mask substrate;
- a viewing window may be fitted to (over) the opening in the mask substrate, such as at a location corresponding with the patients mouth when the facemask is fitted to the patient's face. The viewing window may comprise a clear (transparent) material to allow the user to see into the patient's mouth while performing the procedure. The viewing window may be more rigid than the mask substrate.
- One or more openings (instrument ports) may be provided in the mask, such as in the mask substrate portion (rather than in the viewing window) to allow the user to introduce instruments, such as a micro-abrasive sand blaster, into the patient's mouth, to perform the desired procedure.
- A "face conforming" elastic band may be incorporated into a peripheral portion of the mask substrate to help "contour" the mask to the patient's face
- Some "fastening elastics" may be used to attach the mask to (mount/hold the mask onto) the patient's face. One of the fastening elastics may extend around the back of the patient's neck. Two other fastening elastics may extend around the patient's ears.

According to the invention, generally, a dental mask (M) may comprise a very flexible mask substrate (MS) with a relatively rigid front plate (FP) which may be a viewing window (VW) causing the mask substrate to extend forward from a patient's face, forming a chamber in front of the patient's mouth. Instrument ports (IP) on the mask substrate or front plate (FP) allow instruments to be introduced through the mask into the patient's oral or nasal cavity to perform dental or medical procedures. A face-conforming elastic band (CE) on the mask substrate for conforming the mask to contours of the patient's face. A malleable metal strip (MM) for conforming the mask to the patient's nose. The conforming elastic (CE) may extend from opposite ends of the metal strip (MM). Methods of fabricating the mask are disclosed. The mask, and variations thereof, may be used to perform various treatments, including non-oral procedures. Means for using a nebulizer in conjunction with the mask is disclosed, wherein the nebulizer is supported independently of the mask.

According to some embodiments of the invention, a mask (M, FC) for performing medical or dental procedures on a patient may comprise: a relatively flexible mask substrate (MS); at least one elastic strap (CE; FE) for (i) shaping the mask substrate to the patient's face and for (ii) securely and comfortably holding the mask on the patient's face; a relatively rigid front plate (FP), which may be a transparent viewing window (VW) disposed on a front portion of the mask substrate; and one or more instrument ports (IP) extending through the mask substrate or front plate for allowing a user to introduce a device or instrument through the mask into the patient's oral or nasal orifices, to perform a procedure. The ports may be disposed on either side of the front plate (or viewing window).

The front plate may comprise a transparent viewing window positioned on the mask substrate to be located in front of the patient's mouth when the mask is being worn, to allow the user to see well into the patient's mouth during performing a procedure.

Filters (F) may be incorporated into the mask substrate or on the front plate to facilitate patient breathing and to balance pressures between the inside of the mask and the environment A malleable metal strip (MM) having two opposite ends may be disposed across the mask substrate at a position corresponding with the patient's nose. Opposite ends of the conforming elastic (CE) may be attached to the respective two ends of the malleable metal strip.

Deflectors which are "wing" like extensions of the front plate may extend towards the instrument ports to urge the ports forward, making them more accessible.

A door (TD) may be disposed over a port for selectively exposing (opening) or blocking (closing) the port. The door may comprise a fixed component with an opening and a sliding component with an opening. The door may be initially closed (when the openings are not aligned with each other); and the door a may be capable of being opened (when the openings are aligned). A door may be opened either manually, or automatically by the user inserting an instrument or device into the port.

The mask substrate may be initially flat. The mask substrate may be initially in the form of a tapered tube.

The mask may be provided with an adapter for accepting a nebulizer.

The mask may be selected from the group consisting of dental mask (FIG. 1), nasal swab mask (FIG. 9), oral swab mask (FIG. 10), instrument mask (FIG. 11), scope mask (FIG. 12), sinus mask (FIG. 13), bronchoscopy mask (FIG. 14)

According to some embodiments of the invention, a mask (M) for fitting onto a patient's face when performing oral or nasal procedures may comprise: a very flexible mask substrate (MS) having at least one instrument port (IP) in the mask substrate for allowing a user to insert instruments through the mask substrate; and at least one elastic band having a first face conforming portion (CE) for maintaining a relatively secure fit of the facemask on the patient's lower face, including jaw, and a fastening portion (FE) for mounting the mask to the patient's face. A view port (VP) and viewing window (VW) may be provided on the mask substrate for allowing the user to see into the patient's oral cavity. A nose strip (MM) may be provided for conforming the mask substrate to the patient's nose. At least one filter (F) may be attached to the mask substrate. A rigid front plate (FP) may be disposed on the mask substrate. At least one filter (F) may be attached to the rigid front plate, or to the flexible mask substrate. At least one instrument port (IP) in the mask substrate or front plate for allowing the user to insert instruments into the patient's oral cavity or to deliver medications to the patient wearing the mask.

According to some embodiments of the invention, a method of performing a dental or medical procedure on a patient may comprise: mounting a mask on the patient's face, said mask having a very flexible mask substrate and elastics (FE, CE) for mounting and conforming the mask to the patient's face; and providing means, such as a headband or eyeglasses to be worn by the patient, external to the mask itself, to support devices such as a nebulizer.

According to some embodiments of the invention, a mask (M) for performing medical or dental procedures on a patient may comprise: a very flexible mask substrate (MS) portion which conform well to the contour of a patient's face; a relatively rigid portion (FP, VW) disposed at the front of the mask; and at least one instrument port (IP) extending through the relatively rigid portion or the flexible mask substrate portion; wherein: instrument ports (IP) are disposed on the relatively rigid portion; and the relatively rigid portion can be moved around by a user while the flexible mask substrate portion remains fixed in position on the patient's face.

According to some embodiments of the invention, a dental mask (M, DM) for covering at least a patient's mouth while an oral procedure is being performed by a user (dentist) may comprise: a mask substrate (MS) comprising a generally rectangular, flat sheet of a material that is big enough to fit over the patient's lower face and which is very flexible to allow the mask to conform well to the contour of the patient's face; a view port (VP) in the mask substrate; a viewing window (VW) on the view port, and comprising a transparent material which is more rigid than the mask substrate. one or more openings (instrument ports, IP) provided in the mask substrate to allow the user to introduce instruments into the patient's mouth, to perform the procedure; a face conforming elastic band (CE) incorporated into a peripheral portion of the mask substrate to help "contour" the mask substrate to the patient's face; and one or more fastening elastics (FE) for mounting the mask on the patient's face, said fastening elastics extending around the back of the patient's neck or around the patient's cars.

According to some embodiments of the invention, a mask for fitting onto a patient's face when performing oral procedures may comprise: a mask substrate having at least one opening for corresponding at least one viewing window; at least one viewing window installed over the at least one opening: at least one instrument port in the mask substrate for allowing a user to insert instruments through the mask into the patient's mouth; and at least one elastic band having a first face conforming portion for maintaining a relatively secure fit of the facemask on the patient's lower face, including jaw, and a fastening portion for mounting the mask to the patient's face.

According to some embodiments of the invention, a mask for fitting onto a patient's face when performing various procedures may comprise: a very flexible mask substrate portion; an elastic band for conforming the mask substrate to the contour of a patient's face; a relatively rigid viewing window providing a user with a view of the patient's facial features; and at least one instrument port in the mask substrate for allowing the user to insert instruments through the mask into the patient's facial orifices (nostrils and mouth). The mask may have at least one port enabling at least one of the following procedures to be performed by a user on a patient: nasal swabbing; oral swabbing; and Endoscopy, Bronchoscopy and GI.

According to some embodiments of the invention, a mask system may comprise: a flexible mask substrate adapted to be fitted to a patient's face; means (such as elastic bands) for mounting the mask on the patient's face and for maintaining a relatively secure (and airtight) fit of the mask on the patient's lower face, including jaw; and a port (opening for inserting external instrumentalities) in the mask substrate. The mask system may further comprise:

separate from the mask itself, means for supporting an external instrumentality such as a nebulizer in close proximity with the mask (such as in front of the mask), with a patient portion of the nebulizer extending through the port so that a treatment may be administered to the patient. The means for supporting may comprise glasses, goggles, a headband, a cap, or the like to support the nebulizer independently of the mask.

Some of the masks disclosed herein may be referred to as an "Oral Flex Cab" or "Flex Cab", and it should be understood that the applicant may claim trademark rights to "Oral Flex Cab" or "Flex Cab", whether or not these terms are used herein in quotation marks.

The terms "mask", "face mask", "dental mask", "dental facemask", and variations thereof may be used interchangeably herein. Generally, the finished product may be referred to as "mask", or "facemask", while the main component to which other components may be attached (incorporated into the finished mask) may be referred to as the "mask substrate".

In some of the embodiments disclosed herein, a relatively rigid "front plate" (FP, which in some cases is a transparent viewing window VW) may be incorporated onto the front of the relatively flexible mask substrate (MS), and may support other elements such as filters, ports, adapters, etc., and the front plate may not need to be transparent.

In embodiments of the mask which cover the patient's nose, a malleable metal strip may be disposed on the mask substrate which can be deformed to secure the mask substrate to the patient's highly contoured nose. In these cases, the face conforming elastic may not extend completely around the periphery of the mask. Rather, the face conforming elastic may extend from opposite ends of the malleable metal strip, working together to ensure a reliable fit on the patient's face.

Various embodiments of the invention may be described in greater detail in the discussion that follows (including any appendices that may be attached hereto, or in the priority documents).

These may include the apparatus itself, method of manufacturing the apparatus, and methods of treatment which include using the apparatus. This may also include providing for the interaction of the mask with other instrumentalities, such as a nebulizer, which may be supported by independent (of the mask) means such as a headband or glasses worn by the user (of the mask—i.e., the patient). Alternatively, the nebulizer may be hand-held, not requiring the additional support.

Other objects, features and advantages of the invention(s) disclosed herein may become apparent in light of the following illustrations and descriptions thereof.

BRIEF DESCRIPTION OF THE DRAWINGS

Reference will be made in detail to embodiments of the disclosure, non-limiting examples of which may be illustrated in the accompanying drawing figures (FIGS.). The figures may generally be in the form of diagrams. Some elements in the figures may be stylized, simplified or exaggerated, others may be omitted, for illustrative clarity. Some figures, such as "FIGS. #A" and "#B" may be referred to collectively as "FIG. #".

Although the invention is generally described in the context of various exemplary embodiments, it should be understood that it is not intended to limit the invention to these particular embodiments, and individual features of various embodiments may be combined with one another. Any text (legends, notes, reference numerals and the like) appearing on the drawings are incorporated by reference herein.

Some appendices (Appendix 1, Appendix 2) are included with the priority filings (provisional US patent applications), and may be cross-referenced herein.

Figure 1A:
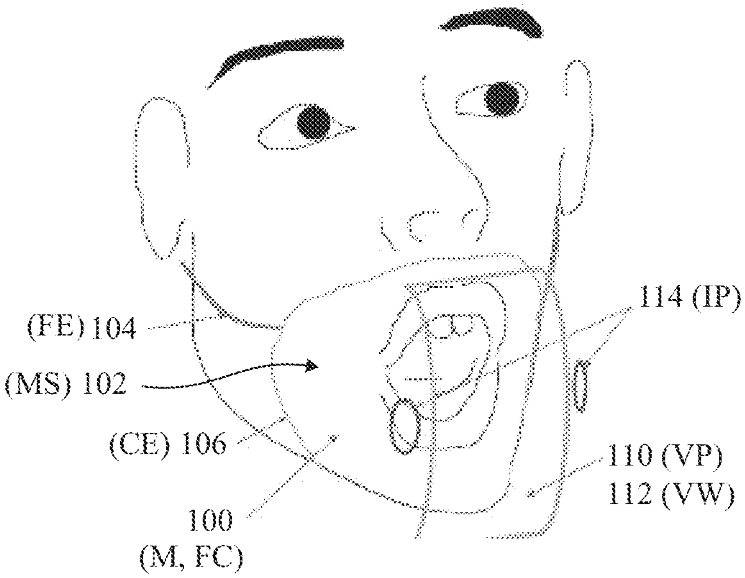

FIG. 1A (Appendix 1, page 1) is a perspective view of the dental mask, mounted to a patient, according to an embodiment of the invention.

Figure 1B:
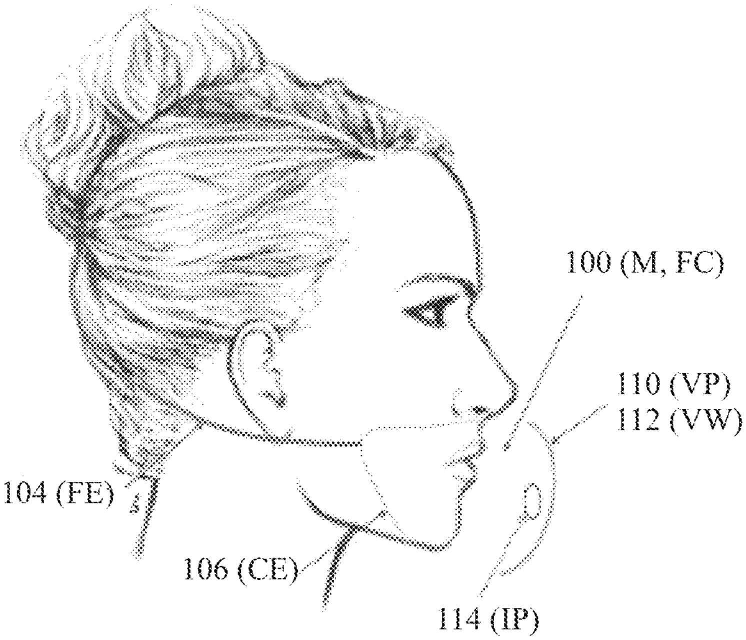

FIG. 1B (Appendix 1, page 1) is a side view of the dental mask, mounted to a patient, according to an embodiment of the invention.

Figure 2A:
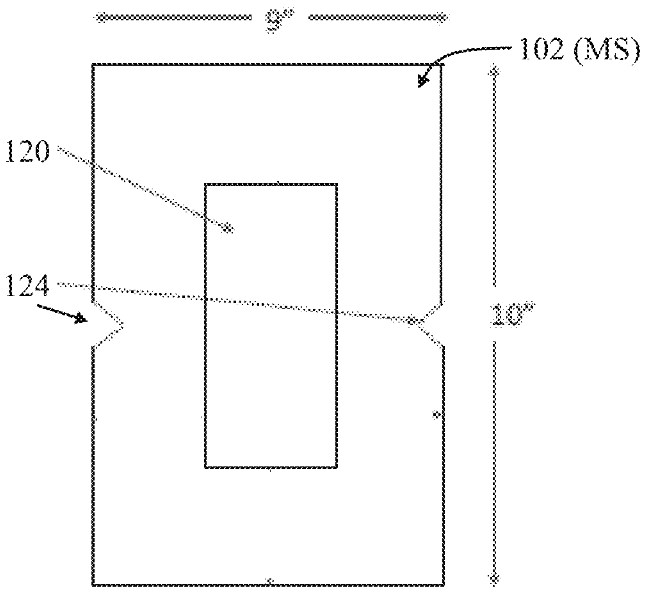

FIG. 2A (Appendix 1, page 3) is a diagram illustrating a first step (Step 1) in the process of manufacturing the mask, according to an embodiment of the invention.

Figure 2B:
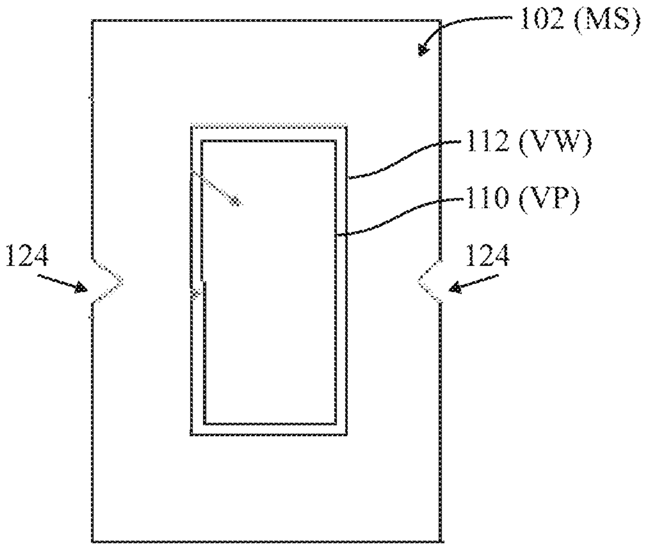

FIG. 2B (Appendix 1, page 3) is a diagram illustrating a next step (Step 2) in the process of manufacturing the mask, according to an embodiment of the invention.

Figure 2C:
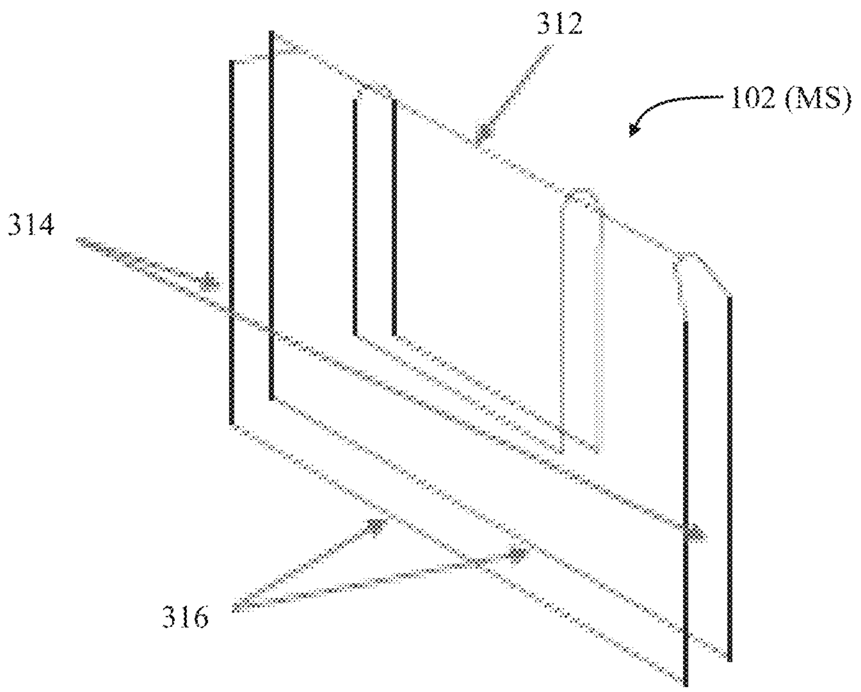

FIG. 2C (Appendix 1, page 4) is a diagram illustrating a first step (Step 3) in the process of manufacturing the mask, according to an embodiment of the invention.

Figure 2D:
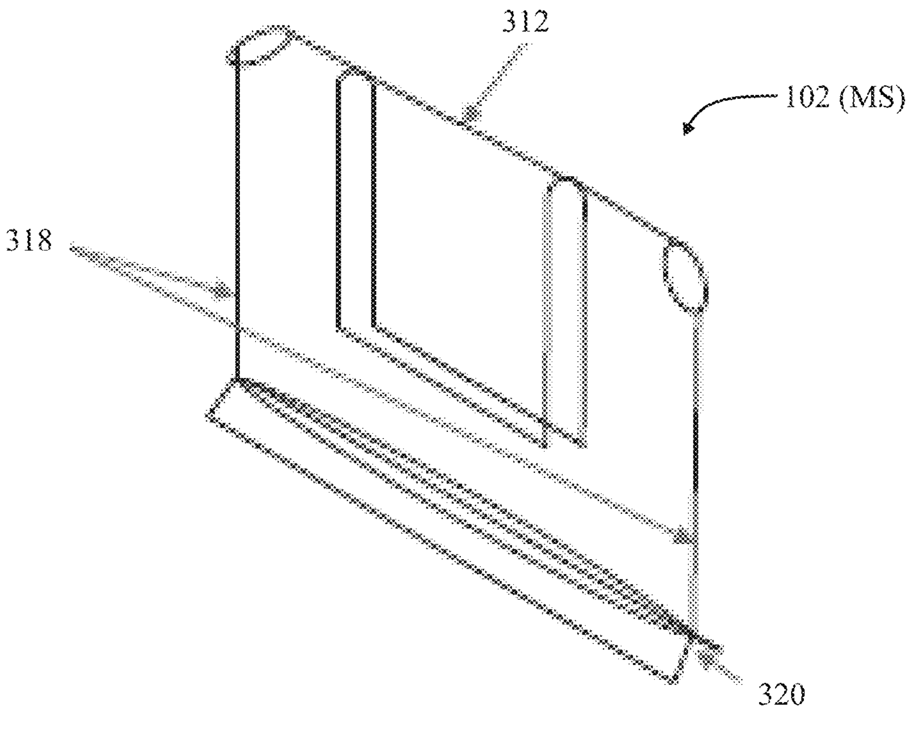

FIG. 2D (Appendix 1, page 4) is a diagram illustrating a next step (Step 4) in the process of manufacturing the mask, according to an embodiment of the invention.

Figure 2E:
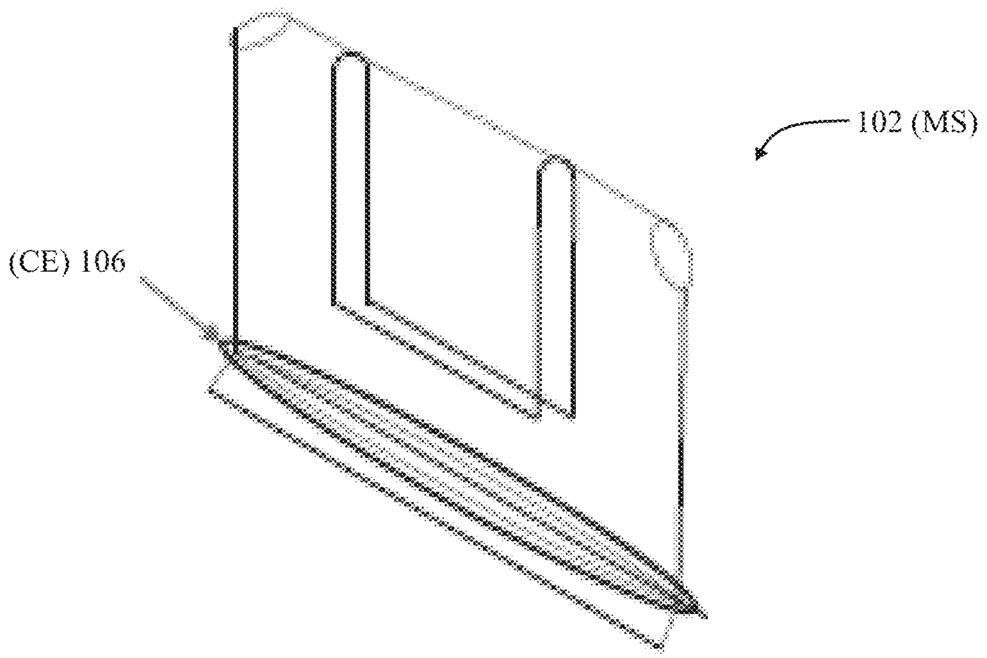

FIG. 2E Appendix 1, (page 5) is a diagram illustrating a first step (Step 5) in the process of manufacturing the mask, according to an embodiment of the invention.

Figure 2F:
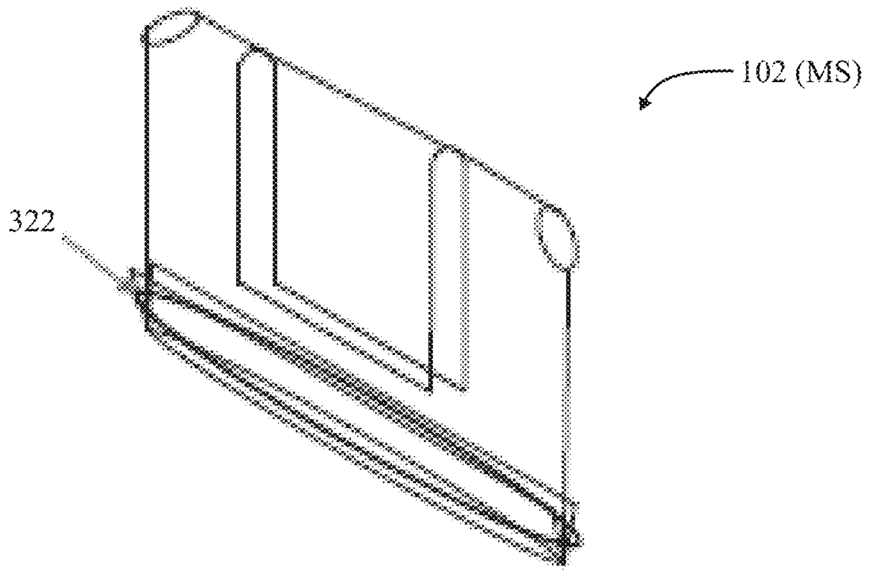

FIG. 2F (Appendix 1, page 5) is a diagram illustrating a next step (Step 6) in the process of manufacturing the mask, according to an embodiment of the invention.

Figure 2G:
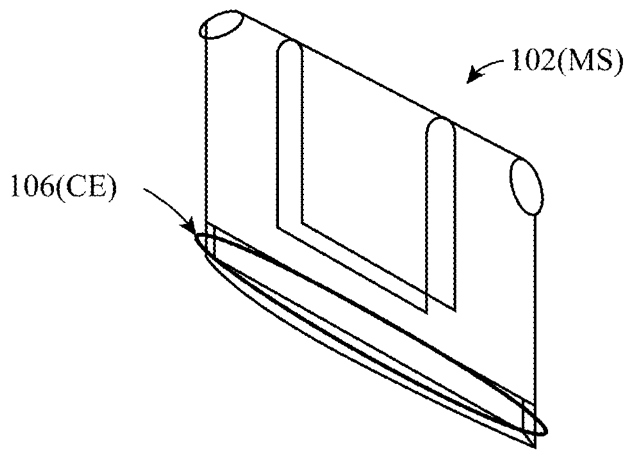

FIG. 2G (Appendix 1, page 6) is a diagram illustrating a first step (Step 7) in the process of manufacturing the mask, according to an embodiment of the invention.

Figures 1, 2H:
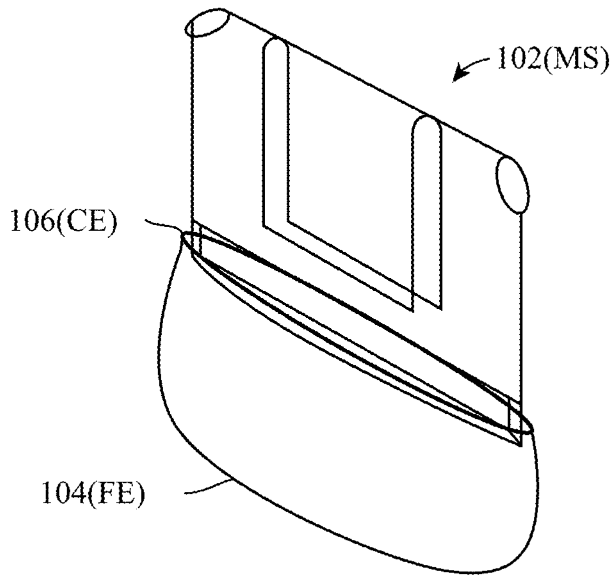

FIG. 2H (2H-1, 2H-2) (Appendix 1, page 6) is a diagram illustrating a next step (Step 8) in the process of manufacturing the mask, according to an embodiment of the invention.

Figure 3A:
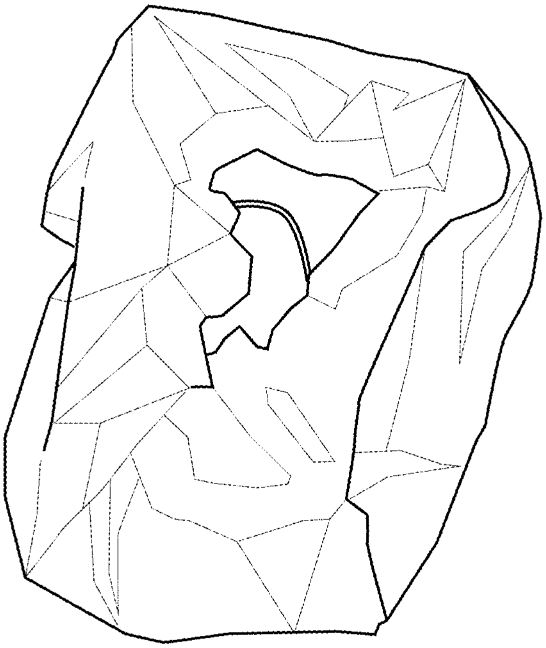

FIGS. 3A, B (Appendix 1, page 7) are front and back side views, respectively, of a completed mask (oral flex cab), such as may have been manufactured as described in the Steps shown in FIGS. 3A-3H, according to an embodiment of the invention.

Figure 4A:
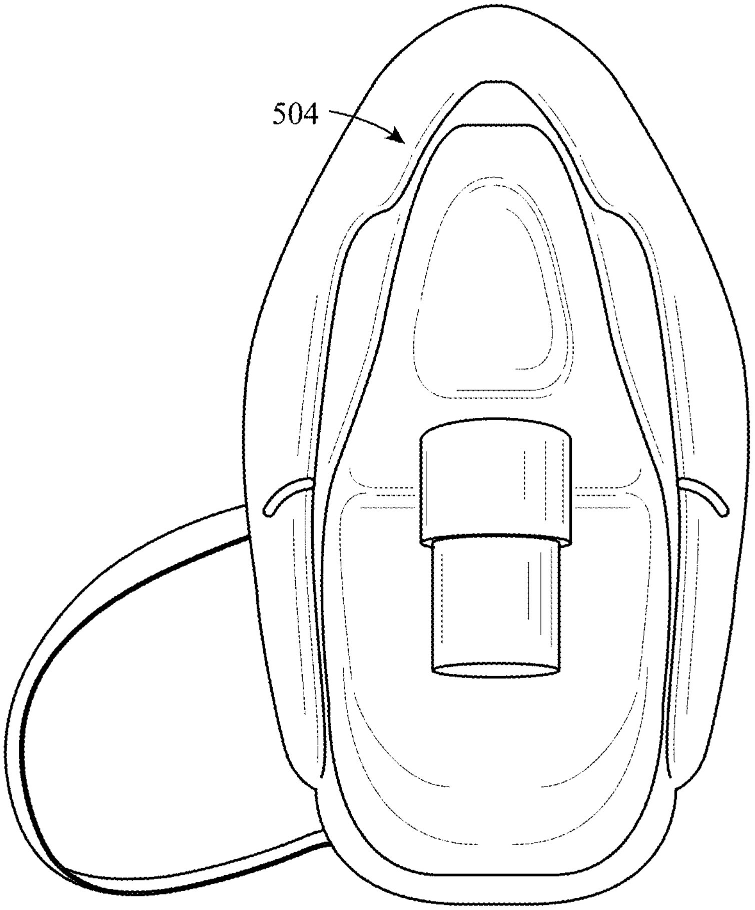

FIG. 4A (Appendix 1, page 8) is a photograph showing an optional forming or shaping feature, such as a malleable metal strip, incorporated at a nose portion of the mask to ensure a better (more snug, more airtight) fit of the mask over the patient's nose, according to an embodiment of the invention.

Figure 5A:
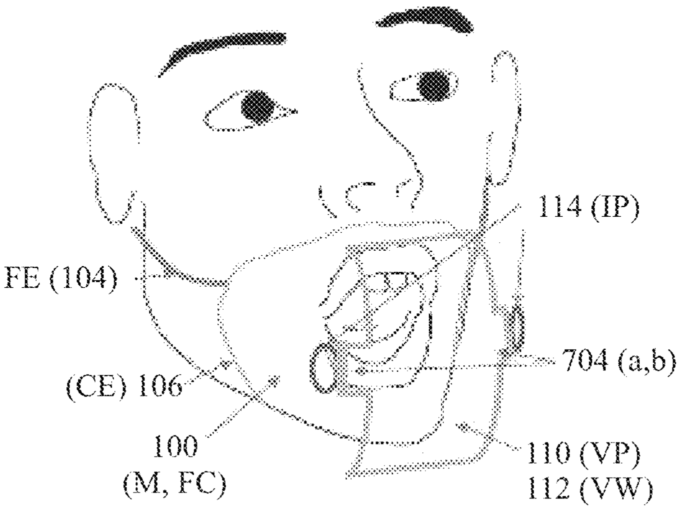

FIGS. 5A, B (Appendix 1, page 9) are sketches (frontal view) showing the mask on a patient's face, and an optional 'Instrument Port Deflector' feature, according to an embodiment of the invention.

Figure 5B:
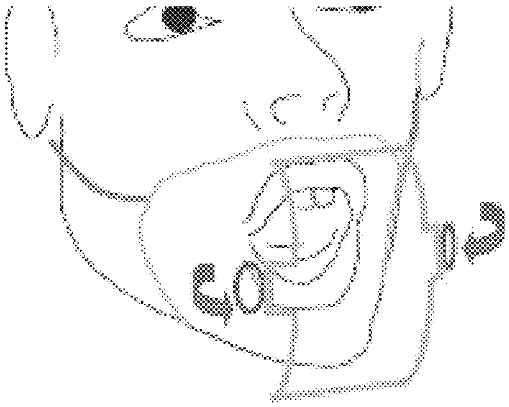
Figure 5C:
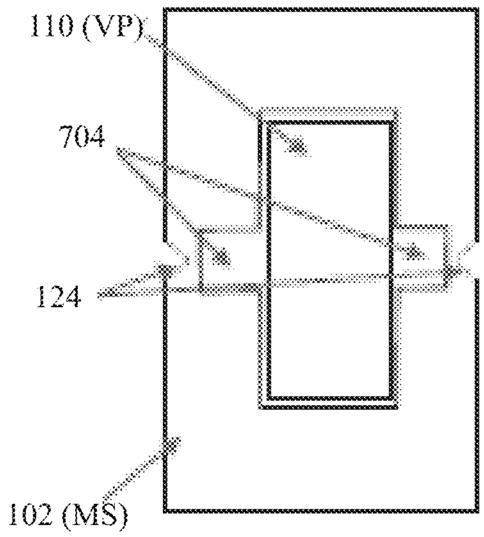
Figure 7:
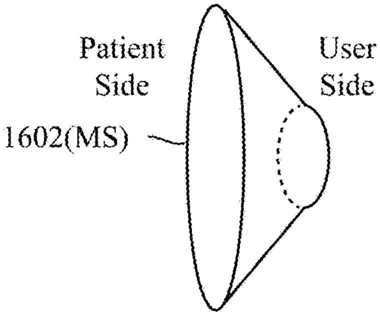
Figure 7F:
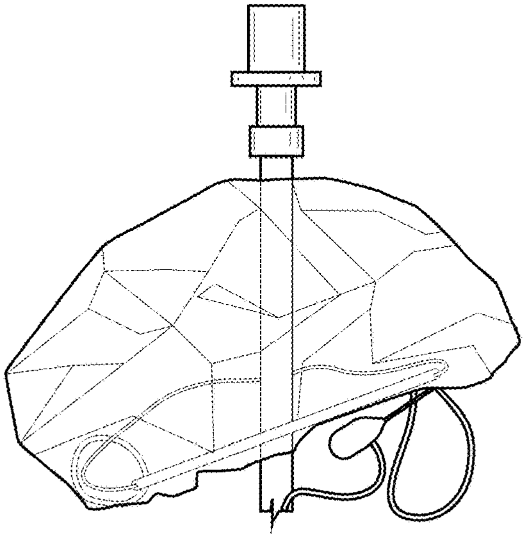
Figure 7A:
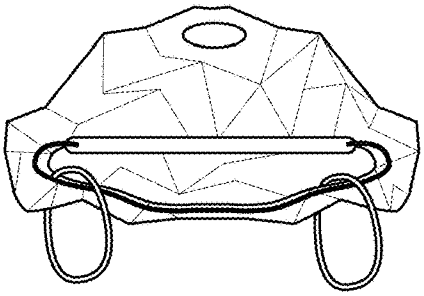

FIGS. 5C, D (Appendix 1, page 9) are diagrams (plan view) showing details of the optional 'Instrument Port Deflector' feature shown in FIGS. 7A, B, according to an embodiment of the invention.

Figure 6:
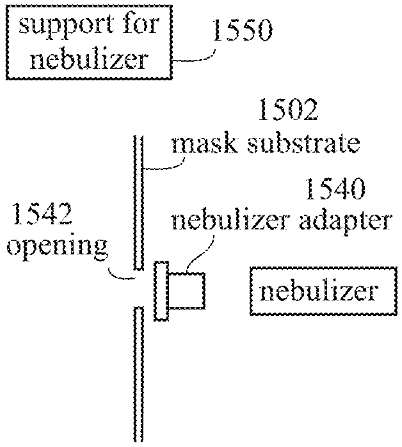

FIG. 6 is a diagram of an adapter for connecting a nebulizer (or the like) to the face mask, according to an embodiment of the invention.

Figure 6A:
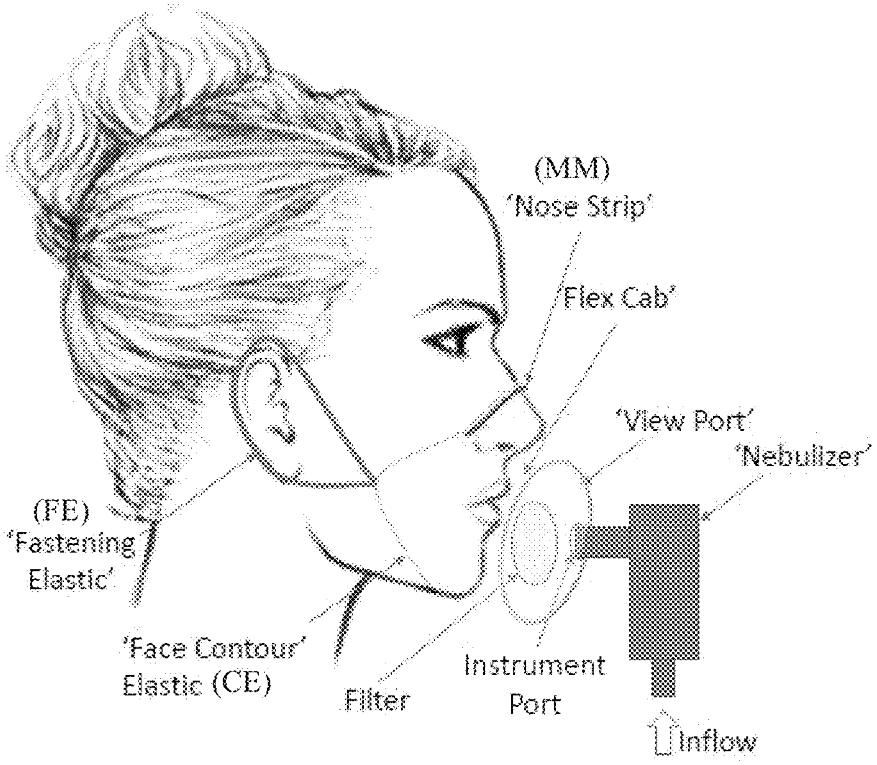

FIGS. 6A, B are diagrams (illustrations) of a patient wearing a mask and receiving a nebulizer treatment, according to some embodiments of the invention.

FIG. 7 is a diagram (side view) a tapered-tube type mask, generally, according to an embodiment of the invention.

FIGS. 7A-F are photographs of a mask, using a tapered (very thin) plastic tube (aka bag) as the mask substrate (MS), as may be suitable for some of the mask embodiments disclosed herein, according to an embodiment of the invention.

Figure 8:
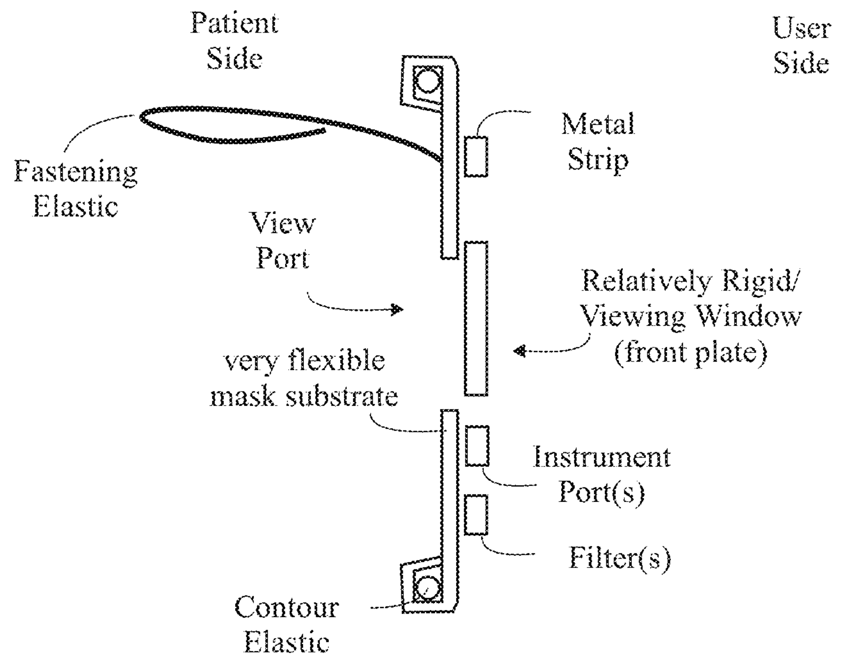

FIG. 8 is a schematic illustration (cross-section, partially exploded) of a "basic" embodiment of a mask, such as a dental mask, according to an embodiment of the invention.

Figure 8A:
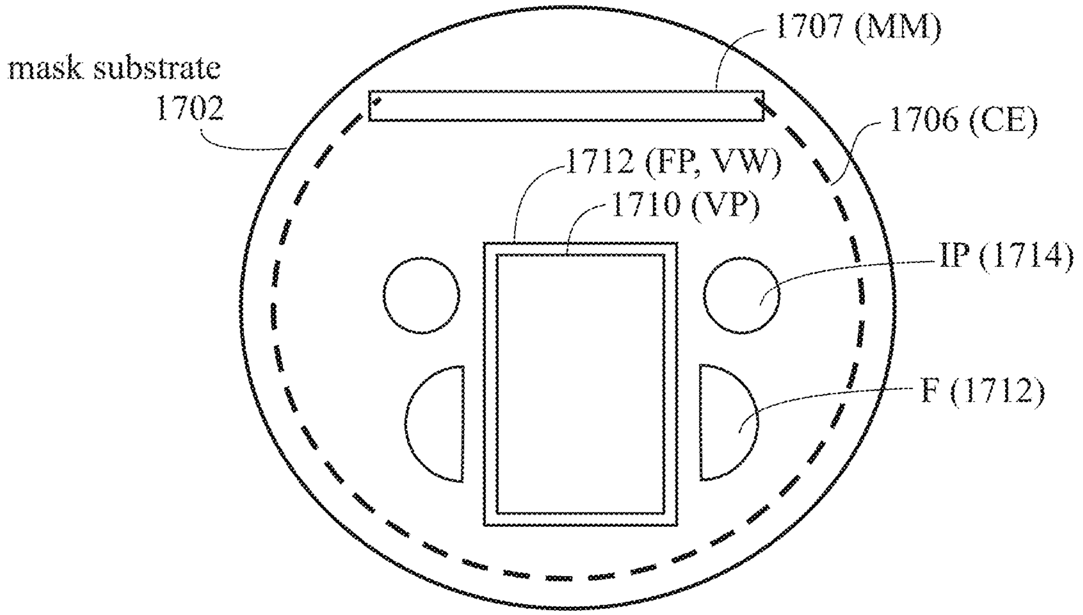

FIG. 8A is a schematic illustration (plan view) of a malleable metal nose strip (MM) integrated with a face conforming elastic (CE), on a "generic" (basic) face mask, according to an embodiment of the invention.

ABBREVIATIONS

Some of the following abbreviations may be used, in the text and/or drawings, in lieu of or in addition to reference numerals.

M overall mask (aka "flex cab" FC)

DM a dental mask (mask specific for performing dental procedures)

MS mask substrate, typically a very flexible sheet of plastic material

CE contour elastic extending around a periphery of the mask substrate

MM a malleable metal strip for conforming the mask to the patient's nose

FE fastening elastic for securing the mask to the patient's head (face)

VP view port, which is an opening at the front of the mask

FP front (or face) plate, which is a rigid element disposed at the front of the mask VW viewing window (a transparent front plate), disposed over the view port P a port (i.e., opening in the MS or in the VW) for inserting something into the mask IP instrument port, which is a specific type of port for inserting an instrument TD a door disposed over a port for exposing (opening) or blocking (closing) the port F filter, which may be mounted either on the MS or on the VW NA nebulizer adapter which may be mounted on the mask to receive a nebulizer

Description

Various embodiments (or examples) may be described to illustrate teachings of the invention(s), and should be construed as illustrative rather than limiting. It should be understood that it is not intended to limit the invention(s) to these particular embodiments. It should be understood that some individual features of various embodiments may be combined in different ways than shown, with one another. Reference herein to "one embodiment", "an embodiment", or similar formulations, may mean that a particular feature, structure, operation, or characteristic described in connection with the embodiment is included in at least one embodiment of the present invention. Some embodiments may not be explicitly designated as such ("an embodiment").

Some dimensions may be set forth herein. These are meant to be exemplary, not limiting, and are intended to convey a sense of scale, and may highlight the relative sizes of different elements (i.e., some larger than others, for example). Some exemplary materials may be set forth herein.

The facemask (or simply "mask") disclosed herein solves both dental and medical needs for the containment of aerosol generated in procedures that require access and visibility into the oral (and nasal) cavity. Such procedures may include, but are not limited to tongue lacerations, tooth and Peritonsillar abscess drainage—all dental procedures (including cleaning), oral exam throat inspection ("say ahhh"), swabbing throat or nose for viral testing, and intubation procedures. Masks for other purposes are also disclosed herein.

Facemasks for oxygen and nebulizing typically have a semi-rigid formed structure and are made of compliant material that somewhat conform to facial contours. They have no features that provide access and visibility into the oral cavity.

Some of the mask embodiments disclosed herein have a viewing window allowing the user (e.g., dentist) to see clearly into a patient's oral cavity while providing access to insert instruments (drills, mirrors, ultrasonic scalers and swabs, etc.) and flexibility to manipulate these instruments without impeding or limiting the user's (i.e., dentist's) motion or visibility. These masks may be referred to as "dental masks".

The dental mask disclosed herein provides a barrier to aerosol generated by the instrumentation (such as during dental procedures) or expelled by the patient (such as coughing), restricting (substantially reducing) aerosol propagation to the environment, thereby reducing the exposure to healthcare providers (dentists, doctors, etc.). These may be referred to as "dental masks". The dental mask (and some of the other masks disclosed herein) may or may not cover the patient's nose.

Other embodiments may have one or more ports for inserting instruments (such as swabs, an endoscope, etc.), through the mask, and generally do not require a clear view into the patient's mouth at all times. These masks may be referred to as "scope/instrument masks".

For a scope/instrument mask, the mask's visibility clarity is not a big concern since once the scope/instrument is in the nasal or oral cavity the user (doctor) may be watching a scope camera. Therefore, the viewing window of a dental mask is not required. The overall mask (mask substrate) may be formed of a clear plastic material which allows sufficient visibility for initial penetration and subsequent extraction of a tool (such as an endoscope).

Generally, all of the embodiments disclosed herein may have:

- a flexible mask substrate which forms the overall mask (flex cab);
- straps (such as elastic bands) for (i) shaping the mask substrate and for (ii) securely and comfortably holding the mask on a patient's face; and
- one or more ports for allowing a user (doctor) to introduce a device or instrument through the mask into a patient's oral or nasal orifices, to perform a procedure. In some cases, the port(s) may initially be closed (such as with a "trap door"), and subsequently the port may be opened by the user either "manually", or "automatically" by the user inserting an instrument or device into/through the port.

The dental mask embodiment has a transparent viewing window (VW, which may be a transparent font plate FP) positioned in front of the patient's mouth (when the mask is being worn) to allow the dentist to see well into the patient's mouth during performing a dental procedure.

Filters may be incorporated into the mask substrate, or on the viewing window (or the like—i.e., on a front plate which is not a viewing window), to facilitate patient breathing, and to balance pressures between the inside of the mask and the environment to avoid separation of contact of the mask with the patient's facial features. (Pressure imbalance may occur when nebulizer treatment or oxygen is introduced into the mask, also due to patient speaking, sneezing, or coughing, etc.)

Means may be provided to accommodate medical devices such as nebulizers, for example, a nebulizer adapter providing treatment to the patient via the mask (flex cab). Means, such as a headband or eyeglasses, external to the mask itself, may be provided to support such devices, since the overall mask (flex cab) is very flexible and otherwise not able to support the device. Handheld devices, such as mouthpiece ("peace pipe") nebulizers, may be used to provide the treatment, without the external means.

DESCRIPTIONS OF THE FIGURES (FIGS.)

Some appendices (Appendix 1, Appendix 2) were filed with some of the priority documents (i.e., US provisional patent applications), and are expressly incorporated by reference herein.

Some of the figures presented in the Appendices may be reproduced as "stand-alone" figures herein. The correspondence between some of the figures presented herein, and some of the figures in the Appendices, may be noted in some of the description(s) set forth herein.

Dental Mask

FIGS. 1A, B illustrate an embodiment of a dental mask 100, mounted to (fitted to, worn by) a patient, according to an embodiment of the invention. See also Appendix 1, page 1.

FIGS. 2A, B, C show the mask, which may be referred to as "Oral Flex Cab", in use. See also Appendix 1, page 2.

The following elements are shown:

100 mask M (aka flex cab)
102 mask substrate MS
104 fastening elastic FE
106 (face) contour elastic CE
110 view port VP, typically disposed under the viewing window VW
112 viewing window VW, typically disposed over the view port VP
114 instrument ports IP A dental mask 100 may comprise the following elements or components:

- a mask substrate 102 comprising a very thin, very flexible plastic sheet (such as a 1 or 2 mil poly)—preferably (but not necessarily) of clear material—about 10" long and 9" wide. This will form a very flexible "cabinet" (which may be referred to as a "flex cab") in front of the patient's mouth to capture particles coming from the patient's mouth;
- a thicker (more rigid), very clear plastic sheet (such as 7 mil vinyl) about 3.5"×5.5" which will be mounted over a slightly smaller (such as 3"×5") opening 110 in the mask substrate to form a viewing window 112 (the viewing window may sometimes be referred to herein as a "view port");

The viewing window 112 may be disposed over the opening 110 and may be attached (preferably in an air-tight manner) to the mask substrate 102 around the periphery of the opening, by any suitable means (for attaching) such as, but not limited to an adhesive, heat, tape, or ultrasonic welding, etc.;

one or more holes/openings 114 (which may be referred to herein as "instrument ports") may be provided in the mask substrate to permit the user to introduce tools into the patient's oral cavity, for performing a desired treatment. These ports may simply be slits in the mask substrate material, with markings indicating where they are, and they need not be very airtight.

There may be one (or more) instrument ports IP), one located on one side of the viewing window (VW), another located on the other (opposite) side of the viewing window (VW). Alternatively, two instrument ports (IP) could be provided on the same side of the viewing window (VW). Alternatively, the mask may be provided without instrument ports, allowing the user to simply poke instruments through the thin mask substrate (MS), piercing it, to create instrument port hole(s) at desired locations for specialized procedures-such as abscess drainage, where the abscess could require approach from unique angles.

a first, "face contour" elastic band 106 (CE) or the like, disposed around a peripheral portion of the mask substrate (MS) to deform (partially collapse) and hold the otherwise flat and flexible mask substrate around the patient's facial contours, thereby forming a "face-conforming" portion (or end) of the mask;

additional "fastening" elastic bands 104 (FE) or the like to secure (mount, install) the mask to the patient's face by extending around the patient's neck or ears.

The face contour elastic band and additional fastening elastic bands may be integrated to be formed out of a single elastic band, but are discussed separately to provide for description clarity. They may be claimed as "at least one elastic band" for performing the various functions disclosed herein.

Since the viewing window (VW) is made of stiffer plastic than the mask substrate (MS) which is very flexible, when the mask is in place on a patient's face, the viewing window resists bending and therefore pushes back on the thinner mask substrate to create a chamber (i.e., an empty volume) at the front of the mask, in front of the patient's face (particularly mouth) which will allow the user (e.g., dentist) to comfortably manipulate tools inserted through the instrument port(s).

As may be more relevant to some other embodiments, the viewing window may be moved around (back and forth, up and down) relative the patient's face, while the flex cab remains in a fixed position on the patient's face, in which case the viewing window may not need to be transparent, but nevertheless it is provides a rigid platform upon which to mount other things, such as a filter, a trap door, a nebulizer adapter, and the like.

It is apparent, for example in the side view of FIG. 1B, that the viewing window (VW) may be an inch or two (2-5 cm) in front of the patient's mouth. In this, and some other figures, various elements may be designated, and may conform to the description set forth above (FIG. 1A).

Because the mask substrate will become wrinkled at the 'Face Conforming' end (or at the "face cab"), it may acquire a cumulative stiffness which will supports the viewing window and suspends it in front of the patient's oral cavity.

Instruments are easily passed through the instrument port(s) into the oral cavity, while the clear viewing window may be easily nudged (moved slightly) in any direction to permit access and view from various orientations.

In other words, the mask is essentially a very flexible chamber extending from the patient's face, sealed (more or less) around the patients cheeks and jaw, with a window allowing the user to view the patient's oral cavity while permitting tools to be introduced into the oral cavity to perform procedures.

Manufacturing the Mask (Oral Flex Cab)

The mask disclosed herein may be fabricated of simple inexpensive components, it can be manufactured in high volume, and it can be single-use disposable.

FIGS. 2A-H show an exemplary sequence of steps to fabricate the mask (aka 'flex cab'). See also Appendix 1, pages 3-6.

FIG. 2A shows Step 1-flex cab preparation.

FIG. 2B shows Step 2-view port attachment.

FIG. 2A shows a rectangular (or substantially rectangular) sheet of plastic material, such as polyethylene may be prepared measuring, for example, 1-2 mils thick, 9" wide and 10" high (22×25 mm), and may be referred to as the mask substrate (or "cut sheet") 102 (may be referred to as 302).

(a) a relatively large opening 120 ("view port cutout") is prepared in the sheet. This will be the view port 110, and is where the viewing window 112 will be mounted, in the next step. This opening may rectangular, and may be centrally located on the cut sheet. The opening may measure, for example, 3" (7.5 cm) wide and 5" (12.5 cm) high, and:

a top edge of the opening 120 may be disposed at a desired distance from the top edge of the cut sheet, representing a given distance from the patient's upper lip.

a bottom edge of the opening 120 may be disposed at a desired distance from the bottom edge of the cut sheet, representing a given distance from the patient's lower jaw a left edge of the opening 120 may be disposed at a desired distance from the left edge of the cut sheet, representing a given distance from the patient's left cheek.

a right edge of the opening 120 may be disposed at a desired distance from the right edge of the cut sheet, representing a given distance from the patient's right cheek.

(b) cutout openings 124 may be provided on opposite sides of the cut sheet, at approximately halfway between the top and bottom edges of the cut sheet. These cutout openings will provide for instrument access ports 114 on the left and right sides of the finished mask ('flex cab'), as will become evident in a subsequent step. These are shown as small V-shaped notches extending into the substrate from the left and right (as viewed) side edges thereof. A "fold line" (not shown) may extend between the instrument access ports on the left and right sides of the mask substrate. (Step 3 describes folding over.)

It should be understood that the mask substrate may be other than rectangular in that it may have sides that are not straight, tapering towards the top or bottom, etc.

As illustrated by FIG. 2B (Step 2) A viewing window 112 (VW) may be prepared, and may be a rectangular (or generally rectangular, or substantially rectangular) sheet of vinyl measuring, for example, 7 mil thick, 3.5" wide and 5.5" high. The viewing window (112, VW), which is somewhat larger than the view port (110, VP) opening (or cut out) may then be mounted to the mask substrate 102 (MS) over (or under) the view port 110 (VP) with adhesive around the edge of the view port cutout. Alternatively, the viewing window may be welded to the mask substrate using ultrasonic energy or heat. Additionally, the view port cutout window may be of the same or larger dimensions than the view port sheet and glue tape may be used to connect the two component and cover over any gaps between the two components.

It should be understood that the mask substrate (MS) and the viewing window (VW) may be other than rectangular, such as having rounded corners, being oval, etc. The shape of the and corresponding hole in the mask substrate should be substantially the same shape as the viewing window.

It is also not necessary that the viewing window be larger than and overlap the corresponding hole in the mask substrate. When the viewing window is attached to the mask substrate with an adhesive tape, it may indeed be slightly smaller than the corresponding hole in the mask substrate.

FIG. 2C shows Step 3—Folding

FIG. 2D shows Step 4—connecting side edges

The resulting assembly of mask substrate and viewing window (from Step 2) may now be bent (folded over), and the side edges thereof seamed (via heating, or with an adhesive) to create a bag (which may be referred to herein as a 'Flex Cab') having one closed end (the folded end), two sides which are joined together, and one open end. This folding should be done carefully, to avoid creasing the viewing window ('View Port').

FIG. 2C shows the mask substrate (cut sheet) 102 (MS) with instrument access ports on the side edges thereof and with the viewing window (view port) mounted thereto may be folded over, as shown, so that the left and right side edges are substantially aligned with one another and the top and bottom (face conforming) edges are substantially aligned with one another. This step of folding over should be performed by gently bending the substrate and view port, paying particular attention to not creasing or forming a bend line in the view port which would detract from the clarity of the view port. The following features are noted:

312 bend location

314 side edges are aligned

316 "face conforming" edges are aligned

FIG. 2D shows that the side edges of the mask substrate may be connected ("seamed") together, with either heat or an adhesive. Seaming stops about ½" (1 cm) from the face conforming (peripheral) edges of the substrate to facilitate attachment of face-forming elastic (Steps 5, 6). Note that the fold (Step 3) occurred between the left and right side instrument access ports which, when the mask substrate is folded over may become more circular.

312 bend location

318 side edges are seamed together

320 seaming stops about ½" (1.25 cm) from the "face conforming" edges to facilitate attachment of face conforming elastic (CE, not shown).

The top and bottom edges which, as a result of folding over, may also be "seamed" together, with either heat or an adhesive. However, this seaming may occur a small distance, such as ½" inward of the top and bottom edges so that "face conforming" end portions of the top and bottom edges remain free (loose, dangling) to facilitate incorporating a face conforming elastic into the mask, in a subsequent step.

Alternatively, the left and right side edges could be "seamed" together through the entire length and then 'face conforming' end can be folded like a sleeve over the elastic band.

As mentioned above, a bag having three closed sides and an open end may be substituted for a folded over mask substrate with side edges seamed together. The process of bag fabrication could also be utilized where a die and heat sealing punch is lowered over two layers of the mask substrate sheets to attach and cut the sheets where needed, to generate the mask in a single operation.

FIG. 2E (Step 5) shows that a face conforming elastic band 106 may be stretched over the folded substrate 102, extending from side-to-side, just above (inboard of) the free end portions of the top and bottom (as viewed) edges.

FIG. 2F (Step 6) shows that the free end portions 322 of the folded over top and bottom edges of the mask substrate (both shown at the bottom of the folded substrate) are folded upward (as viewed), towards the fold line 312, so that they extend over the face conforming elastic band 106, in preparation for being "captured" by folded-over edges of the mask substrate 102.

FIG. 2G (Step 7) shows that the folded over free end portions of the top and bottom edges, with the face conforming elastic disposed therebetween, are seamed (with adhesive or heat) to capture (secure) the face conforming elastic band 106 (CE) in the mask substrate 102 (MS). The mask substrate is still folded over, in this and the next step.

The purpose of the face conforming elastic band 106 (CE), which is now integral within the facemask, is to provide a force maintaining a relatively secure fit of the facemask on the patient's lower face, including jaw, when the facemask is installed on the patient's face. Separate fastening elastic bands (Step 8) may be incorporated into the facemask to mount the facemask on the patient's face. One elastic band may be used as the face conforming elastic band and the fastening elastic band(s).

An elastic (or rubber) band (which may be referred to herein as 'face conforming elastic') may be mounted to the open end of the folded over mask substrate & viewing window (Steps 3, 4) so that the open side of the bag ('Flex Cab') is flexible with the elastic—such as for head caps—and becomes 'Face Conforming'.

As illustrated, the 'Face Conforming' Elastic is stretched over the 'Flex Cab' at the end of the side seams, and the 'Face Conforming' ends are folded over the elastic. Then the face conforming ends of the mask substrate may be "seamed" to capture the face conforming elastic in a "tunnel" extending along the periphery of the mask substrate.

FIG. 2H (Step 8) shows that two fastening elastics 104 (FE) for mounting the mask to the patient's face.

The left hand figure (FIG. 2H-1) shows a fastening elastic 104 (FE) which is for fastening the facemask via the patient's neck, attached at approximately the location of the side edges "seamed" intersection with the 'face conforming' end.

The right-hand figure (FIG. 2H-1) shows two fastening elastics 104_a_, 104_b_ which are ear loops attached at approximately the location of the side edges "seamed" intersection with the 'face conforming' end.

These two elastics (neck and ears) may be used in conjunction with one another to secure the facemask to the patient's face. And, the aforementioned face-conforming elastic may ensure a good fit of the flat, flexible facemask around the contour of the patient's lower face and jaw.

A single elastic band may be arranged to perform both of the face-conforming and fastening functions of the two elastic bands (CE, FE). Rubber band (or Latex free elastic) may be utilized for contouring (106) to the facial features while softer textured elastic such as the elastic for N95 face masks may be utilized for the ear loops (104, 104*a, b*). These FE elastics may be installed on the mask substrate to hold the resulting flexible mask onto the patient's face, such as by extending around the patient's ears, or the back of their neck.

After fitting the components (view port, conforming/contour elastic, fastening elastics) to the mask substrate, the facemask may be unfolded and ready for use, as shown in FIGS. 4A, B.

The Completed Mask, and Some Optional Features

Figure 3B:
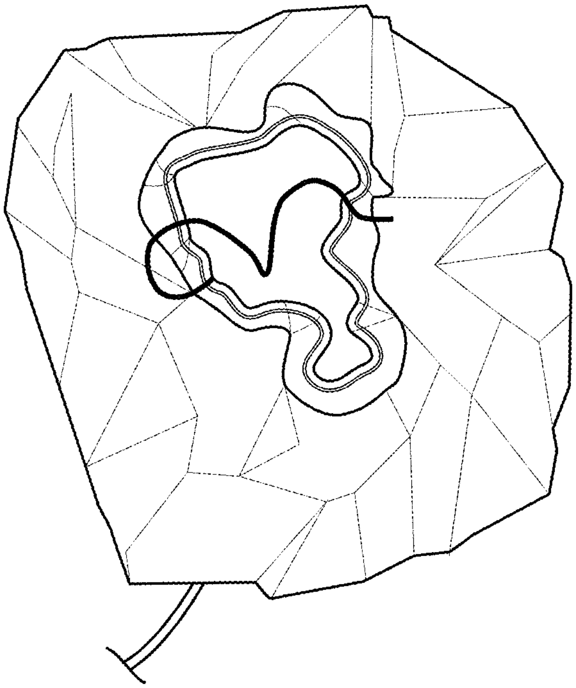

FIGS. 3A, B shows some photographs of the resulting facemask. FIG. 3A shows a view of the front-side of the mask. FIG. 3B shows a view of the back side of the mask.

In use, the face conforming elastic may be pulled to contour to the patient's face by stretching the elastic over patient's jaw/chin via an additional 'Fastening Elastic' band that wraps around the patient's neck (or two additional bands each secures the patient's ears) to position the viewing window ('View Port') in front of the patient's oral cavity.

Some Alternative Steps

Other fabrication steps and/or sequences may be employed to yield substantially the same outcome, such as:

- the viewing window can be attached to the mask substrate first, and then the mask substrate material may be removed to expose the 'View Port', instead of first making a cutout (view port) in the mask substrate. Additionally, the operation can be reversed where the mask substrate is attached to the viewing window.
- starting with a preformed poly bag or tube where the viewing window is mounted in a bend that conforms to the bag shape instead of mounting to a flat sheet (mask substrate) first.
- if a bag is utilized as the mask substrate, the two corners at the closed ends of the bag may be then cut to create the openings (instrument ports) for instrument access.

Some benefits of the mask disclosed herein may include:

- contact may be maintained with the patient's chin/lower jaw when mouth is open and closed, so that the patient can speak and be heard during the procedures;
- permits easy placement of instruments-such as suction devices-between 'face conforming' elastic and patient's skin;
- facilitates easy 'poking' of additional holes for procedures that require access of more than two hands (such as when an assistant is helping the dentist);
- permits the easy manipulation of the cheeks with user's fingers;

Some Optional/Additional Features

For some applications it may be advantageous that the mask (flex cab) covers the patient's nose in addition to the oral cavity.

FIG. 4A (see Appendix 1, page 8) shows that a forming feature 504 may be added to the mask to ensure a better fit of the mask over the protrusion of the patients nose. The forming feature may be a malleable metal strip, such as is common in medical masks, to ensure a good fit onto the patient's nose.

FIGS. 5A, B, C, D show that an instrument port deflector feature 704 may be incorporated into the mask. FIGS. 5A, B are similar to, and "elaborate upon" FIG. 1A. FIGS. 5B, C are similar to, and "elaborate upon" FIG. 2A, showing an exemplary manufacturing step.

Generally, the instrument port deflector feature 704 comprises some extensions (wings) of the viewing window extending to the left and right (as viewed) from the viewing window 112 (VW), in the direction of the nearby instrument ports 114 (IP) which are disposed to the left and right of the view port 110 (VP). The view port 110 may or may not be cut out (enlarged) to accommodate these "wings". Rather, the wings may extend over the surface of the mask substrate (102), adjacent to (to either side of) the view port 110.

The viewing window 112 material is relatively rigid (in contrast with the very flexible mask substrate), and it tends to remain flat, thereby pushing the 'Flex Cab' sheet (substrate) outward, thereby causing the nearby (closely adjacent to the wings of the viewing port) move forward, becoming more visible to the user for easy access.

Figure 5D:
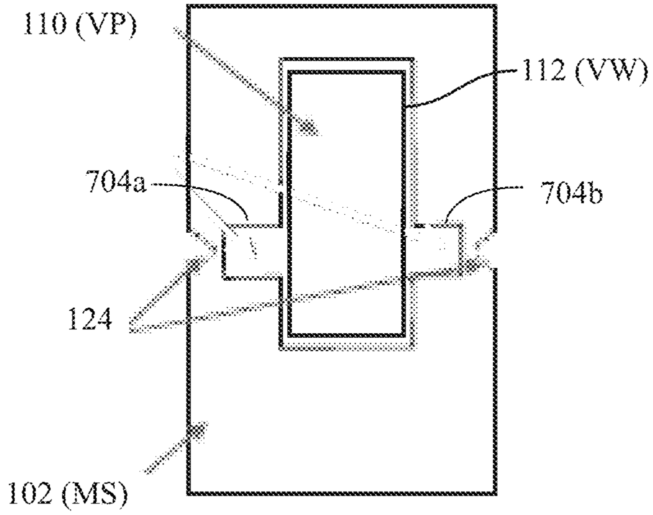

- FIG. 5A shows the deflector features 704 extending from the left and right (as viewed) side edges of the viewing window 112.
- FIG. 5B shows (the curved arrows) how the deflector features 704*a, b* will tend to pull the mask substrate 102 (flex cab) forward, to the left and right (as viewed) sides of the view port (110).
- FIG. 5C shows the deflector features 704*a, b* extending from the left and right side edges, respectively, of the viewing window 112, approximately midway (vertically, as shown) between the top and bottom edges of the mask substrate 102.
- FIG. 5D shows the deflector features 704*a, b* extending from the left and right side edges, respectively, of the viewing window 112. In this example, the deflector features 704*a, b* disposed closer to the bottom (as viewed) edge of the mask substrate 102.

FIGS. 5A, B, C, D (page 9 of Appendix 1) shows the mask ('oral flex cab') mounted to a patient, with the addition of an instrument port deflector. The instrument port deflector may comprise two "wing" portions of the relatively stiff viewing window extending from the left and right sides of the otherwise rectangular viewing window towards the instrument ports located on the respective left and right sides of the relatively soft mask substrate. In use, this will cause the instrument ports to be forced forward a bit. The "logic" behind this is, as follows.

Testing of the mask has shown that it may be difficult at times to identify the 'Instrument Ports' because they may collapse into and be concealed by the wrinkled portion of the very flexible mask substrate (bag).

It therefore may be useful to cause the 'Instrument Ports' 114 to face substantially forward so that the user is able to easily find them and insert an instrument, and so that the ports snap back to that forward position once the instrument is retracted so the user is able to easily identify its location for instrument reinstatement. During user operation of the instrument, this feature should not impede the user's visibility into the oral cavity or interfere with the user's hand and/or instrumentation. That can be established by having a component that causes the mask substrate to expand yet not be in the way of the user, either visually, instrument, or fingers.

To avoid the introduction of new components and processes, the viewing window ('View Port') plastic sheet area may be extended towards the 'Instrument Ports' thereby providing a deflection force near the 'Instrument Ports' thereby forcing the 'Instrument Ports' forward. The 'Instrument Port Deflector' segment(s) of the viewing window does not require a cutout in the mask substrate and is entirely secured to the mask substrate. The viewing window material's tendency is to remain flat thereby pushing the mask substrate sheet outwardly making the 'Instrument Ports' move forward, becoming more visible to the user for easy access.

The overall purpose of the instrument port deflectors (wings) extending from the modified viewing window is to force (urge, distort) the mask substrate outward (away from the patient's face), when the mask is worn by a patient.

Alternatively, modifying the mask substrate itself was considered and tested. This involved creating inflation locations on the mask substrate surface to achieve the desired firmness in the selected areas, such as features on floaties, packing blisters. However, this "solution" was considered to be susceptible to failure if a sharp instrument were to pierce the inflated surface made of the thin poly material.

Some Uses for the Mask

In the parent application, as originally filed, FIGS. 8A, B showed the dental mask, in use during a clinical examination (FIG. 8A) and during a prophylaxis procedure (FIG. 8B). See also Appendix 2, page 1, FIGS. 1A, B.

The mask of FIGS. 1-5 may be referred to as a "dental mask", as it is intended primarily for use by a dentist, and is focused on clear visibility required for dental procedures, and includes a clear 'View Port' enabling a user (e.g., dentist) to see well into the patient's mouth during the entirety of a procedure. In some embodiments the patient's nose is also enclosed with the mask (dental cab, flex cab).

Dentists use UV cure lights for curing bonding materials intra-orally, and they use special UV filtering glasses and protective guards. The mask disclosed herein may be fabricated of UV protection (UV blocking or filtering) plastic, which may eliminate the need for these protective devices to be worn by the dentist. Or, when UV protective plastic is used in conjunction with these devices, increased protection for the dentist may be provided.

Some Variations and Optional/Additional Items/Features

- the instrument entry points (ports) could also be made as slits, or with elastic patches so they wrap tightly around the instruments to increase isolation (air-tightness);
- the opening ('View Port') for the viewing window in the mask substrate (plastic sheet) does not have to be symmetrical with respect to the bend line;
- the 'View Port' may be placed so that its edge is closer to the upper lip and more distant from the lower jaw thereby providing better visibility depending on patient-provider special positioning.
- the 'View Port' positioning may favor one side versus the other (i.e. shifted toward right or left cheek) to accommodate specialized procedures.
- A forming feature, such as a nose strip, may be added to the mask to facilitates better contact with the nose contours.
- A low flow aeration of the viewing window may be provided to remove any condensation that may form on the 'View Port'.
- A wiper feature may be provided to clean off the inside surface of the viewing window in case of water splatter or other fluids impede visibility during the procedure.
- Elastic band to secure the mask to the patient can be integral to the mask 'face conforming' elastic, so one piece of elastic is used for 'face conforming' and attachment around the patient's neck or ears.
- A filter can be incorporated into the mask to reduce bag inflation for procedures that generate increased air pressure in the mouth—such as air abrasive or air polishing procedures—or patient sneezing.

- A filter can be mounted to the mask to reduce bag collapse for procedures that generate decreased air pressure in the mouth-such as dental irrigation suction-filter permits pressure equalization on both sides of the mask so there is no mask deformation.
- For nasal swabbing procedures, one or more instrument access ports(s) can be disposed in the mask substrate around the nasal cavity.
- For intubation type procedures, the instrument access port(s) in the mask may be positioned central to the oral cavity with the viewing window, or a plurality of viewing windows disposed on the mask substrate. These viewing windows may be located offset from the center of the mask.
- An empty balloon bag (like an oxygen mask reservoir bag) may be attached to the mask to capture high air flows due to sneezing thereby reducing the likelihood of aerosol spread through the 'instrument ports' and 'face conforming' end of the mask due to back pressure. Such balloon bags are standard equipment for oxygen masks.
- The mask may have an evacuation port for the attachment of aerosol capturing devices, such as air purifiers, evacuation and suction devices.
- The mask may be used as a containment chamber for aerosol supplied medications.

Some Benefits of the Mask May Include:

- because the mask substrate is very flexible (and "oversized"), the view port (viewing window) may be moved (shifted) around to different positions on the mask substrate, rather than centered thereon, to permit operation on a specific oral quadrant;
- Access via a specialized tool (intubation is a good example where the tool always has a specific orientation and handling yet requires visibility on a specific side of the oral cavity)
- The mask may accommodate a right-handed or left-handed healthcare provider
- The mask may accommodate specialized instrument holding (such as hygiene procedures)
- The mask may provide for coverage of the nose area when there is the potential of sneezing, such as when performing nose or throat swabbing.

Some Additional (Other) Mask Embodiments

Some other masks, similar in many respects to the dental mask described above, will now be described. Generally, many or all of the mask embodiments disclosed herein may utilize the basic flexible, preferably transparent mask substrate with face contour elastic and fastening elastic(s), as described with respect to the dental mask of FIGS. 1-8. Generally, in these additional (or other) mask embodiments, the view port and viewing window may not be needed, and other features may be incorporated into the mask to permit the user access to the patient's oral or nasal cavities for performing medical procedures such as swabbing, endoscopy, etc.

Nasal Swab Mask

In this embodiment, a trap door is disposed on the mask, rather then the aforementioned viewing window (of the Dental Mask embodiment).

In the parent application, as originally filed, FIGS. 9A, B, C showed a nasal swab mask, a key feature of which may be a so-called "trap door" 900 which can be opened and closed. The trap door may comprise a fixed component 902 with an opening (not visible in FIG. 9A, slightly visible in FIG. 9B)

in it, and may be affixed to the mask substrate 102 in a manner akin to that of the viewing window (VW) in the dental mask. The fixed component may be formed of a rigid plastic material (e.g., PVC, polyethylene, polypropylene, nylon), and need not be transparent. See also Appendix 2, page 2, FIGS. 2A, B, C. The trap door may alternately be mounted to a flat plastic piece akin to the viewing window (VW).

The trap door further comprises a movable component 904 which may be situated and supported to slide back-and-forth over the fixed component 902, alternately exposing and concealing the opening in the fixed component. The movable component may comprise a portion which has an opening 906 in it, and another portion which does not have an opening in it. Actually, the "trap door" shown is more like a sliding door, than a trap door which may typically be a hinged door.

In a given ("open") position of the movable component with respect to the fixed component, the opening in the movable component may line up with (be directly over) the opening in the fixed component so that a user has access to the patient's face, such as for obtaining a nasal swab.

In another ("closed") position of the movable component with respect to the fixed component, the opening in the movable component is not lined up with the opening in the fixed component. Rather, the portion of the movable component without an opening blocks the opening in the fixed component so that aerosols and/or particles expelled or exhaled by the patient wearing the mask are contained within the mask.

A typical swab may be in the form of an elongated plastic member (a handle, or stick), having a mass of cotton or the like at its distal (far) end, in the manner of a Q-Tip™, only longer.

It may be noted that the openings in each of the fixed and movable components may be "keyhole" shaped, a major portion of the opening being round, and a small "slot" portion of the opening extending radially outward from the major portion.

In the parent application, as originally filed, FIG. 9A showed that the trap door may normally be closed, so the opening in the fixed component 902 is blocked by the porting of the moveable component 904 which does not have the opening 906 so that aerosol exhaled by the patient wearing the mask is contained within the mask prior to specimen collection.

In the parent application, as originally filed, FIG. 9B showed that the trap door may be opened to allow a swab tip to pass therethrough. The openings in the fixed and movable portions may be circular, having a diameter of approximately 1.5 inches (38 mm) to avoid contact with the swab tip when it is inserted or withdrawn (i.e., passes) through the trap door (i.e., the aligned openings in the movable and fixed components when the movable component is in the "open" position). FIG. 9B shows that a swab handle may fit into the slots in the openings in the fixed and movable components.

In the parent application, as originally filed, FIG. 9C showed that the trap door may be closed, during performing the desired procedure (e.g. swabbing the patient), with the smaller, radially extending portion of the opening being sufficiently large for the handle of the swab. This minimizes passage of air through the opening(s). In other words, the trap door is closed to create a secure fit over the swab handle for a tight seal during specimen collection.

In the parent application, as originally filed, FIGS. 9A, B, C described a "sliding" version of a trap door. It is within the scope of the invention that the fixed component has the aforementioned keyhole shaped opening, and that the movable component is simply a door (without an opening) which is hinged to the fixed component so that in the "open" position the opening in the fixed component is accessible, and in the "closed" position, it is not.

Oral Swab Mask

In the parent application, as originally filed, FIGS. 10A, B showed an Oral Swab Mask 1000 according to an embodiment of the invention. See also Appendix 2, page 3, FIGS. 3A, B.

This mask has two ports:

- a first port 1030 which may be a trap door, such as a hinged (rather than sliding) door, for inserting a Tongue Depressor; and
- a second port 1032 which may be an opening for inserting a swab.

Oral swabbing may be a two-handed procedure, one of the user's hands manipulating a tongue depressor and the other of the user's hands manipulating the swab. Protecting the user from aerosols/particles in the patient's exhalations are of paramount importance.

In the parent application, as originally filed, FIG. 10A showed the mask with the first port closed. Both ports are normally closed so that aerosol (patient's exhaled air) is contained, prior to specimen collection.

In the parent application, as originally filed, FIG. 10B showed the mask with the tongue depressor inserted into the first (trap door) port, and with the swab extending through the second port. Insertion of the tongue depressor opens swab port trap door so there is no contact with the swab.

Instrument Mask

In the parent application, as originally filed, FIGS. 11A, B showed an Instrument Mask 1100 according to an embodiment of the invention. See also Appendix 2, page 4, FIGS. 4A, B, now FIGS. 3A, B.

This embodiment is similar to the nasal swab mask shown in FIGS. 9A, B, C, in that is may be in the form of a sliding "trap door". In this embodiment, there is a rubber flexible aperture 1002 with a small port (hole) 1004 (contrast the slot in the openings in the nasal swab mask), which may be selectively blocked or accessible using the trap door.

In the parent application, as originally filed, FIG. 11A showed the port is normally closed so that aerosol exhaled by the patient is contained within the mask, prior to specimen collection.

In the parent application, as originally filed, FIG. 11B showed that the trap door may be opened (lifted), exposing an instrument port.

Scope Masks (Endoscopy, Bronchoscopy and GI)

In the parent application, as originally filed, FIGS. 12A, B, C showed a Scope Mask, according to an embodiment of the invention. See also Appendix 2, page 5, FIGS. 5A, B, C. (see FIG. 4A)

This embodiment has a rubber port 1214 mounted to the mask substrate 1202 (alternatively to a separate plastic piece like the viewing window of the dental mask), for performing endoscopy procedures.

This endoscope type mask works with both the rigid scopes and flexible scopes where the instrument has a rubber interface (port) that wraps around the scope. (A finger cot or condom would also work.) The port may be covered, pre-use. The rubber port may optionally be pre-punctured to provide an entry start point for the instrument. The rubber is mounted to the inside of the mask and may be lubricated (with KY gel or other medical lubricant) for smooth movement of the scope through the port. The port has a seal over the port externally (not shown here) assuring that the gel does not dry or get contaminated pre-use. The port is located in vicinity of the nasal passages.

In the parent application, as originally filed, FIG. 12A showed the mask, pre-procedure. The rubber port may be lubricated and covered pre-use.

In the parent application, as originally filed, FIG. 12B showed the mask, with an instrument inserted.

In the parent application, as originally filed, FIG. 12C is an instrument port view from the inside of the mask with the instrument inserted.

Sinus Mask

In the parent application, as originally filed, FIGS. 13A, B show a Sinus Mask, according to an embodiment of the invention. See also Appendix 2, page 6, FIGS. 6A, B.

An endoscopy procedure may be described. The mask has a port for inserting an endoscope. The port may be similar to or substantially the same as the previously described port (1214), but located on the mask substrate (1202) more appropriately to access the patient's nasal passage. Compare FIG. 12C in the application as originally filed.

In the parent application, as originally filed, FIG. 13A showed performing an endoscopy procedure using a rigid scope inserted through the port in the mask.

In the parent application, as originally filed, FIG. 13B showed performing an endoscopy procedure using a flexible scope inserted through the port in the mask.

Bronchoscopy and GI Endoscopy Masks

In the parent application, as originally filed, FIGS. 14A, B, D showed bronchoscopy and GI Endoscopy masks according to an embodiment of the invention. See also Appendix 2, page 7, FIGS. 7A, B, C. The bronchoscopy and GI endoscopy masks may be substantially similar, but may differ in the size of the port since the scopes are of different diameters.

This embodiment of a bronchoscopy and GI endoscopy type mask has the port near the patient's oral cavity and support a port 1414 similar to the port 1214. The port 1414 may be slightly larger in diameter (than the port 1214) to accommodate the wider scopes utilized for these procedures. Compare FIG. 12C of the application as originally filed This embodiment shows filters (F) **1430*a* and 1430*b* on either side of the port 1414. The filters may be semicircular, as shown, having been cut from a standard circular filter, such as a B/V filter. The port and the filters are shown as being disposed on the mask substrate 1402. In this embodiment, there is no more rigid piece such as the viewing window (VW) mounted to the mask substrate (compare MS 102**). The filter shape (semicircular) is a design choice so that the filters do not obscure the user's vision (i.e. up and down vision may be more important than left-right).

In the parent application, as originally filed, FIG. 14A showed a front view of the mask, pre-procedure.

In the parent application, as originally filed, FIG. 14B showed a side view of the mask, pre-procedure.

In the parent application, as originally filed, FIG. 14C showed the mask during a clinical procedure.

Nebulizer Embodiment(s)

The OralFlexCab™ (or "mask") disclosed herein comprises a flexible covering for a patient's face, with bands for fitting the mask to the patient's face (contour elastic) and for securing the mask to the patient's head (fastening elastics), and, and is provided with openings for performing various procedures. FIGS. 1A, B (Appendix 1, page 1) are illustrative of a dental mask.

The dental mask may be adapted (modified) for Nebulizer and Oxygen treatments, in which case the view port and viewing window are not needed. The flexible mask substrate allows for automatically fitting the mask to the contour the facial features and, as described above, various ports may be provided in the mask to allow a user to perform medical procedures while protecting the user from aerosols or particles which may be exhaled by the patient wearing the mask.

It is an object of this embodiment of the invention to provide means for adapting the OralFlexCab™ mask for use with nebulizer and oxygen components. Because the OralFlexCab™ mask is made of thin plastic, external (additional) means such as 'glasses and a hanger' are used for supporting the weight of the nebulizer and oxygen components.

Nebulizers, oxygen components, and the like, may have a mouthpiece that is inserted into the patient's mouth. A problem with this is that the patient may exhale air that bypasses the mouthpiece.

It is an object of this aspect of the invention to capture the patient's exhaled air by using a mask, such as the OralFlexCab™ disclosed herein.

According to an aspect of the invention, generally, separate means (i.e., separate from the mask itself) are provided for adapting a nebulizer or oxygen component, or any device having a mouthpiece, to be used with a flexible mask, such as the OralFlexCab™ disclosed herein. In the main, hereinafter, a nebulizer is described as an exemplary component to be used in conjunction with the mask.

FIG. 6 shows that a nebulizer adapter 1540 may be integrated into the mask substrate 1502, as an instrument port, instead of (for example) a viewing window or a trap door, to allow (accept) a nebulizer (or the like) to be used with the mask. The viewing window may be modified to function as a nebulizer adapter, and need not be transparent. Generally, in some of the embodiments disclosed herein, a relatively rigid "front plate" (which in some cases is a transparent viewing window) may be incorporated onto the front of the relatively flexible mask substrate. The advantages of such a "hybrid" arrangement include that the relatively rigid front plate can be moved around (shifted in position) relative to the patient's face, due to the flexibility of the mask substrate.

The adapter may simply be a tube, with a flange, that fits into an appropriately sized opening 1542 in the substrate (or modified viewing window), and may be glued or welded to the substrate (or modified viewing window). The adapter 1540 may be cylindrical piece of nylon, with a flange, and may be located on an opening 1542 in the mask substrate 1502 and attached (glued, welded) to either the exterior surface of the mask substrate 1502, or on an interior surface thereof (and extend through the opening 1542). Since the nebulizer is a relatively heavy instrument (as compared with the mask itself), separate support means 1550, such as "eyeglasses" or a headband may be provided to support the nebulizer. For a handheld nebulizer, a separate support means may not be required.

As shown in FIG. 15A of the application as originally filed, semi-circular filters (compare **1414*a***) can be fitted to the mask substrate on either side of the nebulizer adapter. These filters are readily available in circular form, and may be referred to as bacterial/viral (B/V) filters. (A B/V filter, as used herein, may resemble a coffee filter.)

In the parent application, as originally filed, FIG. 15A showed that a separate component (support means) such as glasses, goggles, a headband, a cap or the like may be provided, and worn by the patient with a mask, for supporting the nebulizer.

In the parent application, as originally filed, FIG. 15B showed that a hand-held nebulizer may be mounted to the mask, using the adapter, without requiring the separate support means such as was described in FIG. 15A. This may be referred to as NebShield™.

In the parent application, as originally filed, FIG. 15C showed that a hand-held nebulizer may be mounted to the mask, using the adapter, without requiring the separate support means such as was described in FIG. 15A. This may be referred to as NebShield™. The nebulizer instrument supplies aerosolized medication into the mask (flex cab).

In the parent application, as originally filed, FIG. 15D is a detailed (close-up) view of a portion of the NebShield™, showing the contour elastic and the (malleable metal) nose strip.

In the parent application, as originally filed, FIG. 15E is a detailed (close-up) view of a portion of the NebShield™, showing the contour elastic and fastening (ear loop) elastic.

FIG. 6A is an illustration (side view) of a nebulizer instrument supplying aerosolized medication into the mask (flex cab), via an instrument port which may be located in a modified viewing window. The window need not be transparent. A filter is also shown, mounted to the modified viewing window. (Compare FIG. 1B.) This does not require the external support (eyeglass, headband) as shown in FIG. 15A.

Figure 6B:
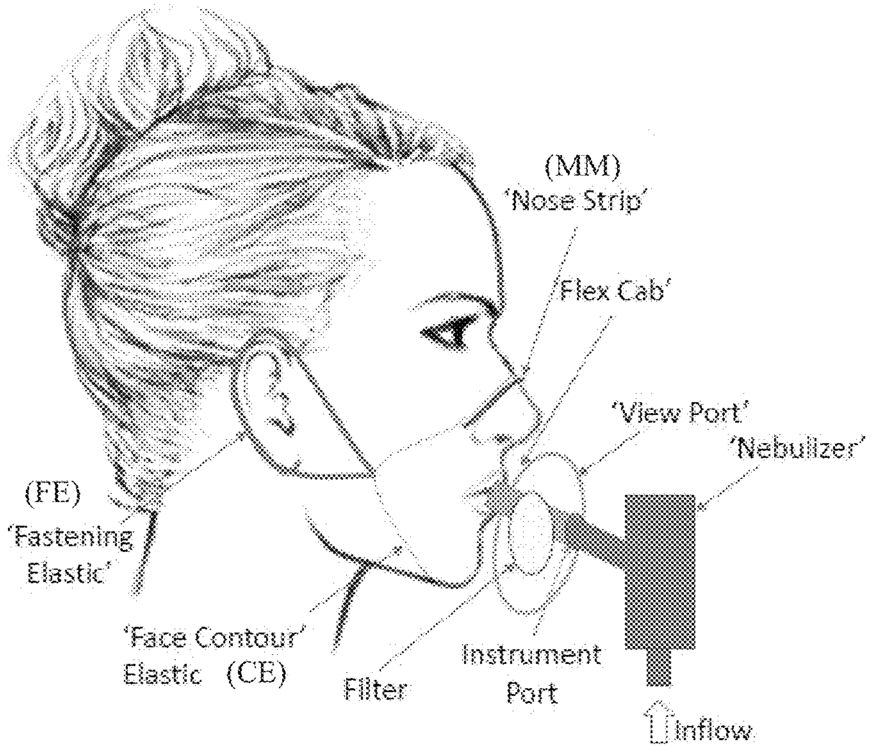

FIG. 6B is an illustration (side view) of a nebulizer instrument supplying aerosolized medication into the mask (flex cab), via an instrument port which may be located in a modified viewing window. The window need not be transparent. A filter is also shown, mounted to the modified viewing window. (Compare FIG. 1B.) This does not require the external support (eyeglass, headband) as shown in FIG. 15A.

Figures 2, 2H:
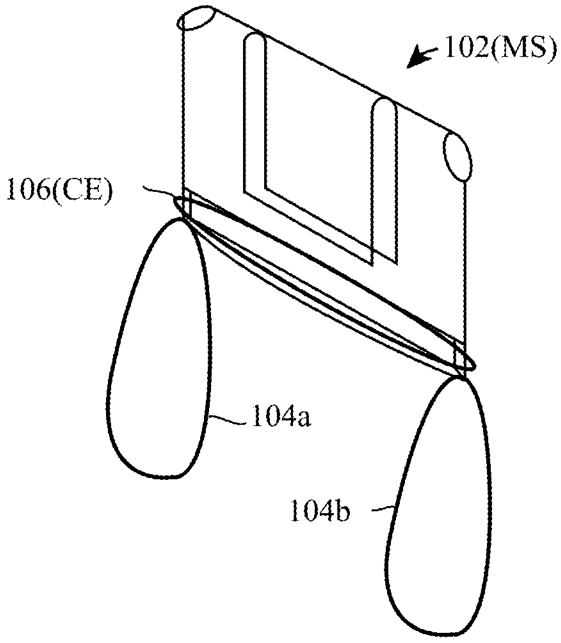

In FIGS. 6A, B, the fastening elastic (FE) is shown as two separate ear loops may be provided (compare FIG. 2H-2). The two ear loops (fastening elastics) may wrap around the patient's ears. Alternatively, a single fastening elastic (FE) may extend from the mask around the back of the patient's head/neck. (compare FIG. 2H-1; also FIGS. 1A, B).

FIGS. 6A, B are shown with a nebulizer, which may be a handheld nebulizer, not requiring the external support (FIG. 15A of the application as originally filed). FIGS. 6A, B also show the malleable metal nose strip (MS) integrated into the mask. FIGS. 6A, B also show a filter disposed on the viewing window (VW, or view port VP), or relatively rigid "front plate" (FP). (A viewing window VW may be considered to be a transparent front plate FP.)

NebShield™ Ports

The NebShield™ may be adapted for use with intubation tubes. The NebShield port (opening, instrument port) is made of a compliant plastic sheet that creates a good seal over a slightly oversized (i.e., slightly larger then the port) predetermined diameter smooth tubes such as nebulizer exhalation tubes.

For use with the i-Gel intubation tubes the NebShield port could be made oval to accept an oval i-Gel device. Since the NebShield port requires a predetermined tube diameter, devices (masks) with specific ports for each size of the i-Gel devices may be made and supplied. Alternatively, the port on the intubation device may be fitted with an elastic band so it fits snugly over (and complies with) various (a range of) sizes of i-Gel devices intubation tubes. Also, since an 'elastic port' expands, it would also work with standard intubation tubes that have a flange at the front end.

Bag Version

FIG. 7 shows a tapered-tube type mask, generally. The mask has a large opening at one end (Patient Side), for fitting to a patient's face, and a smaller opening at the other end (User side) for fitting a front plate, viewing window, instrument ports, trap door, etc. Filters may also be fitted to the mask. Only the mask substrate 1602 (MS) is shown in this figure, for illustrative clarity. Refer, for example, to FIG. 17A for examples of viewing window, instruments ports, filters, etc, disposed on the mask substrate (MS)

FIGS. 7A-F show some examples, and further details, of masks made from a tapered plastic tube as the mask substrate (MS), as may be suitable for some of the mask embodiments disclosed herein.

FIG. 7A is a side view of the mask, showing a tube port (at the small opening end) and a nose strip. Ear loops are shown. The large opening end of the tapered tube may be referred to as the "face end".

Figure 7E:
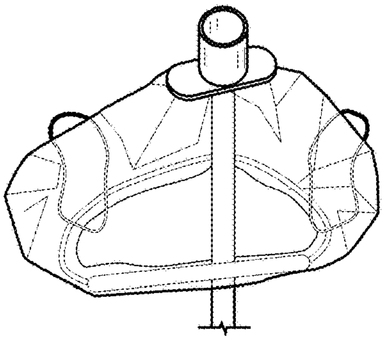
Figure 7B:
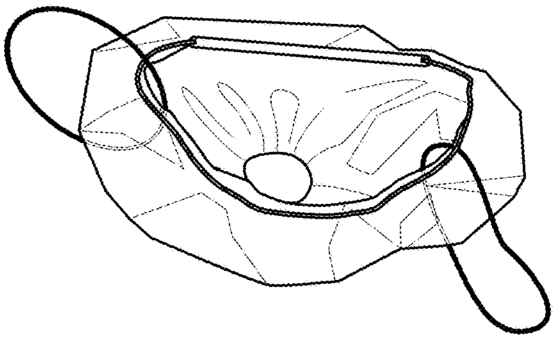

FIG. 7B is a rear view of the mask, and shows elastic bands disposed around the tube port and/or instrument ports. Ear loops are shown.

Figure 7D:
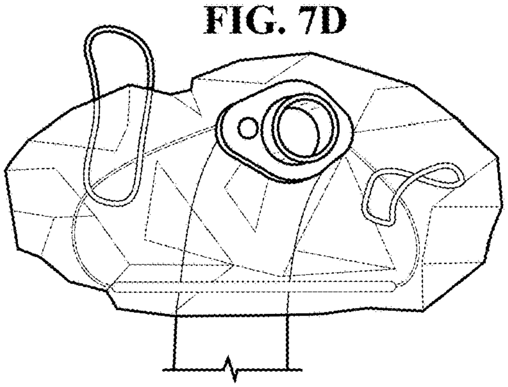
Figure 7C:
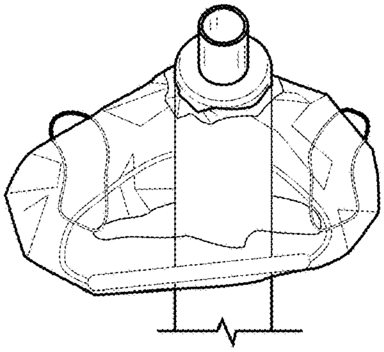

FIG. 7C is a side view of the mask, and shows the small opening end of the tapered tube as an instrument port which fits elastically over an i-Gel device. Ear loops are shown.

FIG. 7D is a front view of the mask, and shows the small opening end of the tapered tube as an instrument port which fits elastically over an i-Gel device. Ear loops are shown.

FIG. 7E is a front view of the mask, and shows a flange (compare . . . ) disposed at the small opening end of the tapered tube, such as for receiving an intubation tube.

FIG. 7F is a side view of the mask, and shows a flange (compare . . . ) disposed at the small opening end of the tapered tube, such as for receiving an intubation tube.

Rather than starting with a flat sheet for the mask substrate (MS), a tapered plastic sheet tube having a larger opening at one end and a smaller opening at the other end may be used at the "starting" material. An elastic band (i.e., contour elastic CE) may be disposed around the large opening of the tapered tube. A nose strip (MM) and ear loops (or fastening elastic FE) may also be incorporated at the large end of the tapered tube (near the larger opening end of the tube). The narrower end of the tapered tube (bag) may be provided an elastic band that fits over and creates a seal with intubation tubes. Filters could be added.

"Basics"

FIG. 8 shows a "basic" (simplified, for illustrative clarity) embodiment of a mask, such as a dental mask, comprising:

- a mask substrate (MS), formed of thin, flexible plastic, which may be transparent. "Patient Side" refers to an interior of the mask. "User Side" refers to the exterior of the mask.
- a view port (opening, VP)) in the mask substrate
- a viewing window (VW) disposed over the view port, on either side of the mask substrate, and formed of a more rigid, transparent plastic. (In some text and/or illustrations herein, the viewing window may be referred to as view port.)
- a fastening elastic (FE) for securing the mask substrate to the user's face
- a face contour elastic (CE) extending around a periphery of the mask substrate for forming the mask to the contour of the user's face. (This is akin to an old-fashioned shower cap—a piece of flexible plastic with an elastic around the edge/perimeter.) When disposed on the patient's face, the mask forms what may be referred to as a "flex cab" (i.e. flexible cabinet), completely closed from the environment by the mask substrate and the user's face.

one of more instrument ports (IP), which are openings in the mask substrate, such as for allowing instruments to be inserted into the flex cab.

one or more filters (F) may be disposed on or in the mask substrate (having a suitable opening for receiving the filter(s). The filters allow air to enter into or exit from the flex cab.

optionally, a malleable metal nose strip (MM) disposed on the mask substrate for forming the mask to the patient's nose In embodiments of the mask which cover the patient's nose, a malleable metal strip (MM) may be disposed on the mask substrate which can be deformed to secure the mask substrate to the patient's highly contoured nose. In these cases, the face conforming elastic (CE) may not extend completely around the periphery of the mask. Rather, the face conforming elastic may extend from opposite ends of the malleable metal strip, working together to ensure a reliable fit on the patient's face.

FIG. 8A shows an example of a mask substrate (MS) 1702 having a malleable metal nose-conforming strip (MM) 1707 "integrated" with the facial contour elastic (CE) 1706. The mask substrate is shown as rounded, and the concept disclosed herein may apply to either the substantially rectangular mask substrate (see, e.g., FIGS. 2A-H), or to the tapered-tubular mask substrate (FIGS. 7A-F).

The malleable metal strip (MM) 1707 is elongated, has two opposite ends, and extends horizontally (as shown) across the mask substrate (MS) at a location that will correspond with the patient's nose, when the mask is being worn. The facial contour elastic (CE) 1706 is elongated, having two ends, and is shown as a dashed line, disposed slightly inboard of the perimeter (periphery, circumference) of the mask substrate 1702. The two ends of the contour elastic (CE) are connected in any suitable manner to the respective two ends of the metal strip (MM).

This "integrated" arrangement of metal strip (MM) and contour elastic (CE) has some advantages. When the mask is worn, the contour elastic (CE) will be stretched over the contour of the patient's face, including nose (in examples of the mask which cover the nose, such as in FIGS. 15F, G). The nose, of course, is a significant (abrupt) protuberance from an otherwise "gently" contoured face. This is why it is advantageous to include the metal strip (MM), such as is commonly found on medical masks. If, for example, the face conforming elastic (CE) were to extend completely around the periphery of the mask (again, we are considering masks that cover the nose here), it would "compete" with the metal strip (MM) for keeping the mask securely mounted to the patient's face.

FIG. 8A also shows an exemplary front plate (FP) 712 disposed on the mask, which may be a viewing window (VW, compare FIG. 1A, 112) disposed over a view port (VP, compare FIG. 1A, 110) in the mask substrate (MS, compare FIG. 1A, 102). FIG. 17A also shows exemplary instrument ports 714 (IP, compare FIG. 1A, 114), and filters 718 (F, compare filters F in FIG. 15A) disposed on the front plate 712, or on the mask substrate near (adjacent, to either side of) the front plate (FP).

Comment(s)

Some differences between the mask(s) disclosed herein and prior art masks is the rigidity of the prior art masks vs. the highly flexible mask (FlexCab™). Many prior art masks do not seal to facial features well, and prior art masks which are made of a more rigid material will tend to move when an instrument inserted therein and the instrument is manipulated, while the more flexible mask disclosed herein will comply as the port in the mask substrate is able to move without disturbing the contact surfaces of the mask with the patient's facial features. (Refer to prior art POM (Procedural Oxygen Mask) masks. https://proceduraloxygenmask.com/)

The masks disclosed herein have a very flexible mask substrate (flex cab), provided with elastics to aid in conforming the mask to the patients face, and more rigid elements (viewing window, ports, etc.) mounted to the mask substrate. In use, the user is able to move (reposition) the more rigid element(s) from their initial position without disturbing the fit or placement of the mask on the patient's face. Hence, the mask(s) disclosed herein are a kind of "hybrid", combining some features of a flexible mask with some features of a rigid mask, while in some cases providing enhanced capability over either a purely flexible mask or a purely rigid mask.

Alternative Uses

It is contemplated that different (or modified) versions of the mask(s) disclosed herein could be used for some non-oral procedures, where access of instruments is required and containment of patient "polluting" fluids may be ejected. For example, incision & drainage procedures for abscess (pus surrounded by inflamed tissue) removal requires guarding of the user/doctor when it is drained. A modified version of the mask can be held to the skin by an elastic band, or a sticky media to prevent fluid splatter. Such modified versions of the mask would have a comparable relatively flexible mask substrate, a relatively stiff viewing window, instrument ports, and means for mounting the mask to the patient.

While the invention(s) may have been described with respect to a limited number of embodiments, these should not be construed as limitations on the scope of the invention (s), but rather as examples of some of the embodiments of the invention(s). Those skilled in the art may envision other possible variations, modifications, and implementations that are also within the scope of the invention(s), and claims, based on the disclosure(s) set forth herein.

What is claimed is:

1. A method of performing a dental or medical procedure on a patient, comprising:

mounting a mask on the patient's face, said mask having a flexible mask substrate and at least one elastic strap for mounting and conforming the mask to the patient's face; and providing the mask with a port and an adapter for accepting a nebulizer;

wherein the mask further comprises:

a rigid front plate (FP) disposed on a front portion of the flexible mask substrate; and wherein:

the port is disposed on a side of the rigid front plate; and a deflector comprising an extension of the rigid front plate extending towards the port.

2. The method of claim 1, further comprising:

providing glasses or goggles, a headband, or a cap to be worn by the patient, external to the mask itself, to support the nebulizer.

3. The method of claim 1, wherein the mask further comprises:

an instrument port (IP) which is configured to allow a user to deliver medications to the patient wearing the mask.

4. The method of claim 1, wherein the mask further comprises:

at least one filter (F) attached to the rigid front plate.

5. The method of claim 1, wherein: the front plate comprises a transparent viewing window positioned on the mask substrate to be located in front of the patient's mouth when the mask is being worn, to allow a user to see into the patient's mouth during performing a procedure.

6. The method of claim 1, further comprising: filters (F) incorporated into the flexible mask substrate or on the rigid front plate to facilitate patient breathing and to balance pressures between the inside of the mask and the environment.

* * * * *